(12) United States Patent
Howlett et al.

(10) Patent No.: US 8,197,749 B2
(45) Date of Patent: Jun. 12, 2012

(54) METHODS FOR CLEANING LUER CONNECTORS

(75) Inventors: Michael W. Howlett, Salt Lake City, UT (US); James V. Mercer, West Jordan, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 574 days.

(21) Appl. No.: 12/171,997

(22) Filed: Jul. 11, 2008

(65) Prior Publication Data

US 2009/0062766 A1    Mar. 5, 2009

Related U.S. Application Data

(63) Continuation-in-part of application No. 12/164,310, filed on Jun. 30, 2008, now Pat. No. 8,177,761, which is a continuation-in-part of application No. 12/014,388, filed on Jan. 15, 2008, now abandoned.

(60) Provisional application No. 60/880,541, filed on Jan. 16, 2007.

(51) Int. Cl.
*A61L 2/00* (2006.01)
*A61L 2/18* (2006.01)
*A61L 9/00* (2006.01)
*A61M 5/14* (2006.01)
*B65D 43/03* (2006.01)

(52) U.S. Cl. .......... 422/28; 422/292; 604/256; 604/500; 604/905; 220/380

(58) Field of Classification Search .................. 604/905, 604/29, 283, 256, 403, 533; 424/292, 28; 220/380
See application file for complete search history.

(56) References Cited

U.S. PATENT DOCUMENTS

| 2,351,804 | A | * | 6/1944 | Bium | 206/3 |
| 2,356,969 | A | * | 8/1944 | Blum | 206/3 |
| 3,315,830 | A | * | 4/1967 | Flynn | 215/334 |
| 3,446,596 | A |   | 5/1969 | Salivar et al. | |
| 3,987,930 | A | * | 10/1976 | Fuson | 220/287 |

(Continued)

FOREIGN PATENT DOCUMENTS

WO    WO 2006/099306    9/2006

(Continued)

OTHER PUBLICATIONS

Curos Port Protector product brochure, circa Nov. 2008, 2 pages, available at http://www.iveramed.com/docs/Curos%20Brochure-FINAL.pdf.

(Continued)

*Primary Examiner* — Kevin C Sirmons
*Assistant Examiner* — William Carpenter
(74) *Attorney, Agent, or Firm* — Sunstein Kann Murphy & Timbers LLP

(57) ABSTRACT

Illustrative pairs of caps are disclosed, each of the caps being sized and shaped to provide a protective union about a separated medical connector. A pair of caps can include a male cap and a female cap, each of which is configured to be coupled to the other cap in an assembly. The assembly is sealed until the caps are separated for use, thereby maintaining sterility of the internal surfaces of the caps. Related methods are also disclosed.

10 Claims, 15 Drawing Sheets

U.S. PATENT DOCUMENTS

| | | | |
|---|---|---|---|
| 4,232,677 A | 11/1980 | Liebinsohn | |
| 4,324,239 A | 4/1982 | Gordon et al. | |
| 4,340,052 A | 7/1982 | Dennehey et al. | 128/247 |
| 4,346,703 A * | 8/1982 | Dennehey et al. | 604/406 |
| 4,354,490 A * | 10/1982 | Rogers | 604/403 |
| 4,369,781 A | 1/1983 | Gilson et al. | 128/214 |
| 4,402,691 A | 9/1983 | Rosenthal et al. | |
| 4,432,764 A | 2/1984 | Lopez | |
| 4,432,766 A | 2/1984 | Bellotti et al. | 604/283 |
| 4,440,207 A * | 4/1984 | Genatempo et al. | 150/154 |
| 4,450,624 A | 5/1984 | Collier | |
| 4,624,664 A * | 11/1986 | Peluso et al. | 604/256 |
| 4,671,306 A | 6/1987 | Spector | 132/73 |
| 4,778,447 A * | 10/1988 | Velde et al. | 604/29 |
| 4,838,875 A | 6/1989 | Somor | |
| 5,205,821 A | 4/1993 | Kruger et al. | |
| 5,242,425 A | 9/1993 | White et al. | |
| 5,466,219 A | 11/1995 | Lynn et al. | |
| 5,536,258 A * | 7/1996 | Folden | 604/265 |
| 5,554,135 A * | 9/1996 | Menyhay | 604/256 |
| 5,694,978 A | 12/1997 | Heilmann et al. | |
| 5,792,120 A * | 8/1998 | Menyhay | 604/256 |
| 5,894,015 A | 4/1999 | Rechtin | |
| 5,951,519 A | 9/1999 | Utterberg | |
| 5,954,957 A | 9/1999 | Chin-Loy et al. | 210/232 |
| 6,045,539 A * | 4/2000 | Menyhay | 604/256 |
| 6,171,287 B1 | 1/2001 | Lynn et al. | |
| 6,932,795 B2 | 8/2005 | Lopez et al. | |
| 6,960,191 B2 | 11/2005 | Howlett et al. | |
| 7,040,598 B2 | 5/2006 | Raybuck | |
| 7,040,669 B2 | 5/2006 | Raybuck | |
| 7,198,611 B2 | 4/2007 | Connell et al. | |
| D547,446 S | 7/2007 | Racz et al. | D24/129 |
| D550,355 S | 9/2007 | Racz et al. | D24/129 |
| 7,316,669 B2 | 1/2008 | Ranalletta | |
| D607,325 S | 1/2010 | Rogers et al. | |
| 7,762,524 B2 | 7/2010 | Cawthon et al. | |
| 7,780,794 B2 | 8/2010 | Rogers et al. | |
| 7,922,701 B2 | 4/2011 | Buchman | 604/256 |
| 7,985,302 B2 | 7/2011 | Rogers et al. | |
| 2002/0093192 A1 | 7/2002 | Matkovich | |
| 2003/0140441 A1 | 7/2003 | Stafford | |
| 2003/0153865 A1 | 8/2003 | Connell et al. | |
| 2003/0198502 A1 | 10/2003 | Maloney et al. | |
| 2004/0201216 A1* | 10/2004 | Segal et al. | 285/401 |
| 2004/0214316 A1 | 10/2004 | O'Connell | |
| 2004/0258560 A1 | 12/2004 | Lake, Jr. et al. | 422/28 |
| 2005/0033267 A1 | 2/2005 | Decaria | |
| 2005/0124970 A1* | 6/2005 | Kunin et al. | 604/508 |
| 2005/0147524 A1 | 7/2005 | Bousquet | 422/28 |
| 2005/0203460 A1 | 9/2005 | Kim | |
| 2005/0245883 A1 | 11/2005 | Baldwin | |
| 2005/0266714 A1 | 12/2005 | Higgins et al. | |
| 2006/0030827 A1 | 2/2006 | Raulerson et al. | |
| 2007/0112333 A1* | 5/2007 | Hoang et al. | 604/533 |
| 2007/0202177 A1 | 8/2007 | Hoang | 424/486 |
| 2007/0287989 A1 | 12/2007 | Crawford et al. | 604/507 |
| 2007/0293818 A1 | 12/2007 | Stout et al. | 604/93.01 |
| 2007/0293822 A1 | 12/2007 | Crawford et al. | 604/175 |
| 2008/0021381 A1 | 1/2008 | Lurvey et al. | 604/85 |
| 2008/0027399 A1 | 1/2008 | Harding et al. | 604/265 |
| 2008/0038167 A1* | 2/2008 | Lynn | 422/294 |
| 2008/0039803 A1* | 2/2008 | Lynn | 604/256 |
| 2008/0086091 A1 | 4/2008 | Anderson et al. | 604/486 |
| 2008/0095680 A1 | 4/2008 | Steffens et al. | |
| 2008/0105704 A1 | 5/2008 | Pritchard | |
| 2008/0107564 A1 | 5/2008 | Sternberg et al. | 422/486 |
| 2008/0132880 A1 | 6/2008 | Buchman | |
| 2008/0147047 A1 | 6/2008 | Davis et al. | 604/533 |
| 2008/0177250 A1 | 7/2008 | Howlett et al. | |
| 2008/0235888 A1* | 10/2008 | Vaillancourt et al. | 15/104.94 |
| 2009/0008393 A1 | 1/2009 | Howlett et al. | |
| 2009/0062766 A1 | 3/2009 | Howlett et al. | |
| 2009/0205151 A1 | 8/2009 | Fisher et al. | |
| 2010/0047123 A1 | 2/2010 | Solomon et al. | |
| 2010/0049170 A1 | 2/2010 | Solomon et al. | |
| 2010/0242993 A1 | 9/2010 | Hoang et al. | |
| 2010/0306938 A1 | 12/2010 | Rogers et al. | |
| 2010/0313366 A1 | 12/2010 | Rogers et al. | |
| 2011/0044850 A1 | 2/2011 | Solomon et al. | |
| 2011/0213341 A1 | 9/2011 | Solomon et al. | |
| 2011/0217212 A1 | 9/2011 | Solomon et al. | |
| 2012/0039764 A1 | 2/2012 | Solomon | 422/292 |
| 2012/0039765 A1 | 2/2012 | Solomon | 422/292 |

FOREIGN PATENT DOCUMENTS

| | | |
|---|---|---|
| WO | WO-2008/089196 | 7/2008 |
| WO | WO-2008/100950 | 8/2008 |
| WO | WO-2010/002808 | 1/2010 |
| WO | WO-2010/141508 | 12/2010 |
| WO | WO-2011/053924 | 5/2011 |
| WO | WO-2011/066565 | 6/2011 |
| WO | WO-2011/066586 | 6/2011 |

OTHER PUBLICATIONS

Hospira Male/Female Sterile Cap product packaging insert and brochure, circa Aug. 2004, 2 pages.

BD Q-Syte Luer Access Split Septum product brochure, circa Nov. 2008, 4 pages, available at http://www.bd.com/infusion/pdfs/D16333.pdf.

Tego Connector product brochure, circa Nov. 2008, 2 pages, available at http://www.icumed.com/Docs-Tego/M1-1148%20TEGO%20Folder%20Brochure%20Rev.3.pdf.

Baxa Corporation Launches PadLock Set Saver for IV Safety press release, Oct. 10, 2007, 2 pages available at http://www.pr.com/press-release/55432.

Baxa Corporation PadLock Set Saver Specifications and Instructions for Use, copyright 2007, 2 pages, available at http://www.baxa.com/resources/docs/5300103905C.pdf.

Baxa Corporation Padlock product brochure, copyright 2007, 1 page, available at http://www.baxa.com/resources/docs/5300104405A.pdf.

Baxa Corporation Padlock Microbial Testing Technical Paper, copyright 2007, 4 pages, available at http://www.baxa.com/resources/docs/technicalPapers/PadLockMicrobialChallengeTechPaper.pdf.

Baxa Corporation Padlock catalog page, 3 pages, copyright 2009, available at http://www.baxa.com/SearchResults/ProductDetail/?id=6452BFB9-3048-7B87-701697FB93902BA6.

*One Less Problem*, Managing Infection Control, Jun. 2008, available at http://www.baxa.com/resources/docs/OneLessProbPaper.pdf.

Unomedical Medical Products catalog, circa Jan. 2006, 2 pages, available at http://www.unomedical.net/au/section05/section10/LocalSSI/..%5C..%5Cpdf%5Cmedical.pdf.

Braun product catalog, circa Aug. 2008, 2pages.

Curos Port Protector web page from http://www.iveramed.com./, dated Jul. 11, 2008, 1 pages.

International Search Report with Written Opinion for International Application No. PCT/US2009/049094 dated Aug. 31, 2009.

Office Action dated May 5, 2009 for U.S. Appl. No. 12/014,388.

Response to Office Action dated Sep. 4, 2009 for U.S. Appl. No. 12/014,388.

Response to Restriction Election dated Feb. 13, 2009 for U.S. Appl. No. 12/014,388.

Office Action dated Nov. 13, 2008 for U.S. Application No. 12/014,388.

Buchman, et al., "A New Central Venous Catheter Cap: Decreased Microbial Growth and Risk for Catheter-Related bloodstream Infection." The Journal of Vascular Access 2009, 10: pp. 11-21.

Notice of Publication of U.S. Appl. No. 12/610,141 dated Feb. 25, 2010.

Notice of Publication of U.S. Appl. No. 12/610,033 dated Feb. 25, 2010.

Office Action dated Jan. 27, 2010 for U. S. Appl. No. 12/014,388.

Response to Office Action dated Apr. 26, 2010 for U.S. Appl. No. 12/014,388.

International Search Report and Written Opinion for PCT/US2009/049094 dated Aug. 31, 2009.

Office Action dated Nov. 13, 2008 for U.S. Appl. No. 12/014,388.

Maki, Dennis G., "In Vitro Studies of a Novel Antimicrobial Luer-Activated Needleless Connector for Prevention of Catheter-Related Blookstream Infection," Clinical Infection Diseases, Jun. 15 2010, vol. 50, Issue 12, pp. 1580-1587.

Curos Port Protector web page from http://www.iveramed.com./, dated Jul. 11, 2008.
Restriction Requirement mailed Nov. 13, 2008 in U.S. Appl. No. 12/014,388, now abandoned.
Amendment and Response to Restriction Requirement filed Mar. 24, 3009 in U.S. Appl. No. 12/014,388, now abandoned.
Interview Summary mailed Sep. 1, 2009 in U.S. Appl. No. 12/014,388, now abandoned.
Office Action mailed May 5, 2009 in U.S. Appl. No. 12/014,388, now abandoned.
Amendment and Response to Office Action filed Sep. 4, 2009 in U.S. Appl. No. 12/014,388, now abandoned.
Notice of Non-Compliance Amendment mailed Sep. 28, 2009 in U.S. Appl. No. 12/014,388, now abandoned.
Amendment and Response to Office Action filed Oct. 2, 2009 in U.S. Appl. No. 12/014,388, now abandoned.
Final Office Action mailed Jan. 27, 2010 in U.S. Appl. No. 12/014,388, now abandoned.
RCE and Amendment and Response to Office Action filed Apr. 26, 2010 in U.S. Appl. No. 12/014,388, now abandoned.
Office Action mailed Jun. 21, 2010 in U.S. Appl. No. 12/014,388, now abandoned.
Amendment and Response to Office Action filed Oct. 19, 2010 in U.S. Appl. No. 12/014,388, now abandoned.
Interview Summary mailed Oct. 25, 2010 in U.S. Appl. No. 12/014,388, now abandoned.
Final Office Action mailed Dec. 23, 2010 in U.S. Appl. No. 12/014,388, now abandoned.
Express Abandonment filed Feb. 15, 2011 in U.S. Appl. No. 12/014,388, now abandoned.
Restriction Requirement mailed May 21, 2010 in co-pending U.S. Appl. No. 12/164,310, now published as US 2009/0008393.
Amendment and Response to Restriction Requirement filed Jun. 21, 2010 in co-pending U.S. Appl. No. 12/164,310, now published as US 2009/0008393.
Office Action mailed Aug. 16, 2010 in co-pending U.S. Appl. No. 12/164,310, now published as US 2009/0008393.
Amendment and Response to Office Action filed Oct. 29, 2010 in co-pending U.S. Appl. No. 12/164,310, now published as US 2009/0008393.
Interview Summary mailed Oct. 25, 2010 in co-pending U.S. Appl. No. 12/164,310, now published as US 2009/0008393.
Notice of Non-Compliant Amendment mailed Nov. 03, 2010 in co-pending U.S. Appl. No. 12/164,310, now published as US 2009/0008393.
Amendment and Reponse to Office Action filed Feb. 16, 2011 in co-pending U.S. Appl. No. 12/164,310, now published as US 2009/0008393.
Notification of Transmittal of the International Search Report and the Written Opinion of the International Searching Authority issued Aug. 1, 2008 in International Application No. PCT/US2008/051087.
Notification of Transmittal of the International Search Report and the Written Opinion of the International Searching Authority issued Jan. 6, 2011 in International Application No. PCT/US2010/054995.
Notification of Transmittal of the International Search Report and the Written Opinion of the International Searching Authority issued Jan. 26, 2011 in International Application No. PCT/US2010/058404.
Notification of Transmittal of the International Search Report and the Written Opinion of the International Searching Authority issued Feb. 7, 2011 in International Application No. PCT/US2010/058453.
Co-pending U.S. Appl. No. 12/917,336 titled Disinfecting Caps and Systems and Associated Methods, filed Nov. 1, 2010.
Co-pending U.S. Appl. No. 29/383,403 titled Capping System for Use With One or More Medical Connectors, filed Jan. 17, 2011.
Co-pending U.S. Appl. No. 12/956,704 titled Disinfecting Caps Having an Extendable Feature and Related Systems and Methods, filed Nov. 30, 2010.
Co-pending U.S. Appl. No. 12/957,263 titled Disinfecting Caps Having Sealing Features and Related Systems and Methods, filed Nov. 30, 2010.
Final Office Action mailed Apr. 22, 2011 in co-pending U.S. Appl. No. 12/164,310, now published as U.S. Publication No. US-2009/0008393.
Preliminary Amendment filed Jun. 13, 2011 in co-pending U.S. Appl. No. 29/383,403.
Preliminary Amendment filed May 13, 2011 in co-pending U.S. Appl. No. 12/956,704.
Preliminary Amendment filed May 13, 2011 in co-pending U.S. Appl. No. 12/957,263.

* cited by examiner

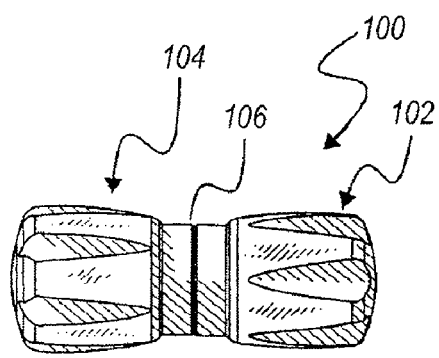
Figure 1
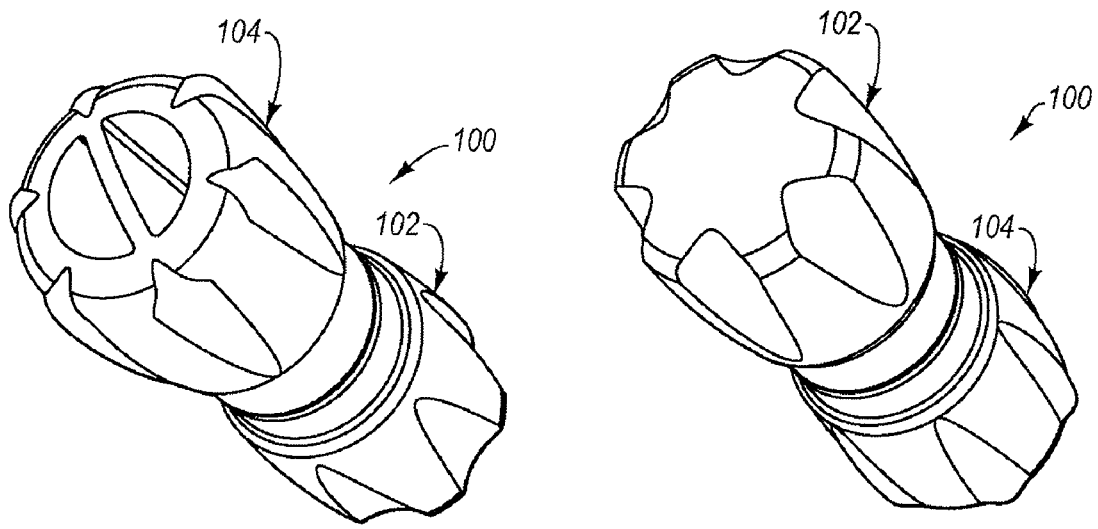
Figure 1A
Figure 1B

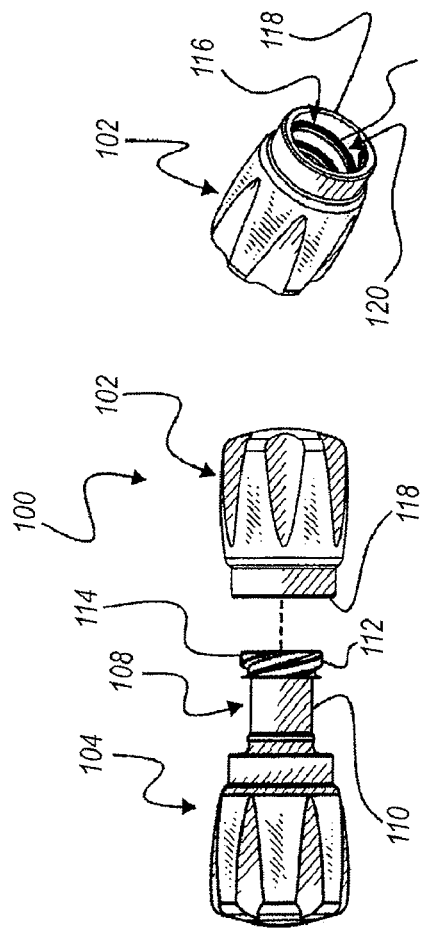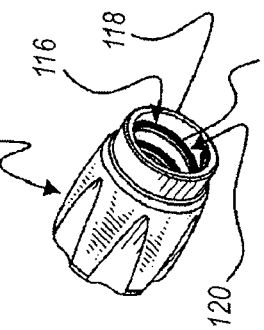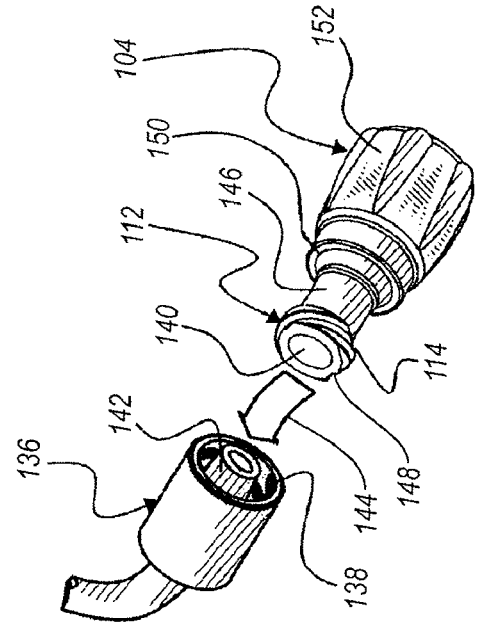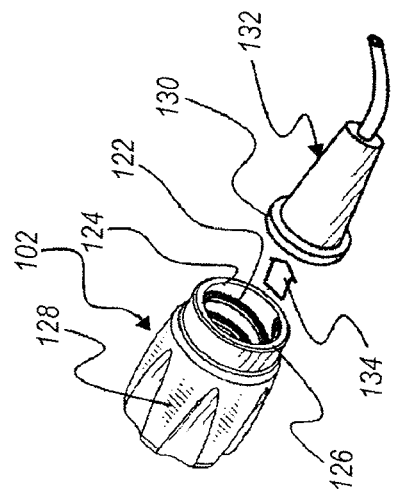

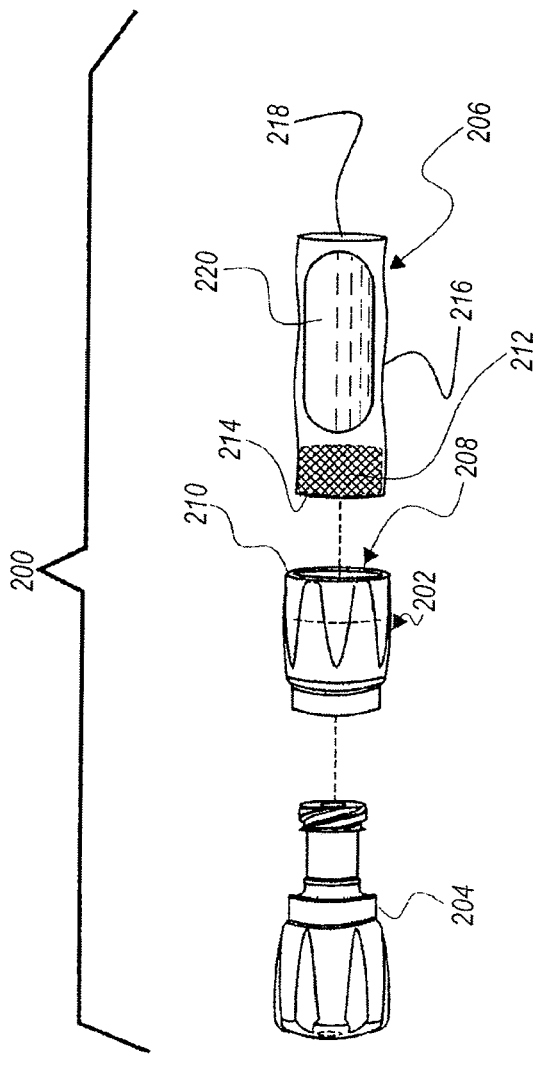
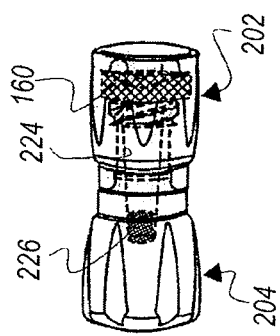
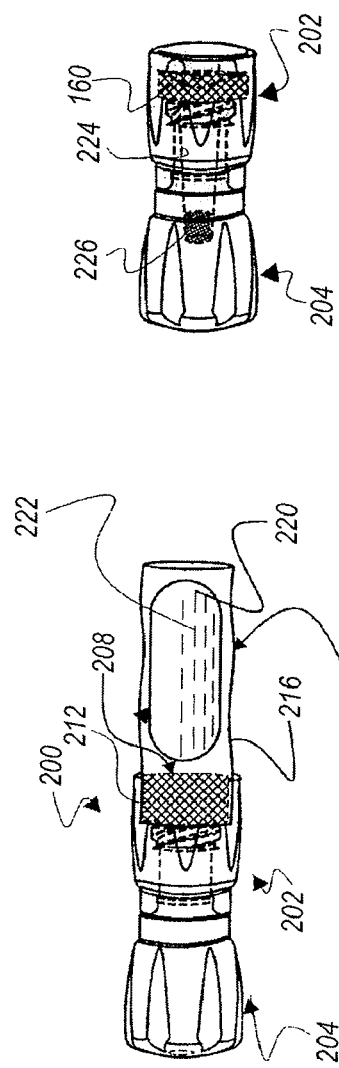
Figure 10
Figure 11
Figure 12

METHODS FOR CLEANING LUER CONNECTORS

CROSS-REFERENCE TO RELATED APPLICATIONS

This application is a continuation-in-part of U.S. patent application Ser. No. 12/164,310, titled NESTABLE STERILITY-PROTECTING CAPS WITH FLUID RESERVOIR FOR SEPARATED CONNECTORS, filed Jun. 30, 2008 now U.S. Pat. No. 8,177,761, which is a continuation-in-part of U.S. patent application Ser. No. 12/014,388, titled NESTABLE STERILITY-PROTECTING CAPS FOR SEPARATED CONNECTORS, filed Jan. 15, 2008 now abandoned, which claims the benefit of U.S. Provisional Application No. 60/880,541, titled ANTISEPTIC PROTECTIVE CAP FOR MALE AND FEMALE SCREW-TOGETHER CONNECTORS, filed Jan. 16, 2007, which are incorporated herein by reference in their entireties.

BACKGROUND

1. The Field of the Invention

This invention is generally related to caps for medical connectors and specifically related to caps used to protect the sterility of separated medical fluid-flow connectors and fluid delivery systems.

2. The Relevant Technology

Catheter-related bloodstream infections are caused by microorganisms in patients with intravascular catheters. These infections are a significant cause of illness and excess medical costs. Approximately 80,000 catheter-related bloodstream infections occur in U.S. intensive care units annually. Additionally, such infections are associated with up to 20,000 deaths per year in the United States alone.

Guidelines from the Centers for Disease Control and Prevention describe various ways to limit catheter-related bloodstream infections in hospital, outpatient and home care settings. The guidelines address issues such as hand hygiene, catheter site care and admixture preparation. However, despite these guidelines, catheter-related bloodstream infections continue to plague our healthcare system at rates essentially unchanged over the past 10 years.

Impregnating catheters with various antimicrobial agents is one approach that has been implemented to prevent these infections. These catheters, however, have given less than satisfactory results. Additionally, some microbes have developed resistance to the various antimicrobial agents.

In another system that is commercially available in Europe, a catheter hub containing an antiseptic chamber is filled with three percent iodinated alcohol. Though it has shown to be effective, the catheter hub is expensive and does not fare as well in a formal cost-benefit analysis.

Caps used for protecting sterility of medical connectors are well known in the medical art. Commonly, protective tip caps are applied to luer connectors of tubing, IV access devices, stopcocks and syringes. Many examples of such tip caps are commercially available. Most commercially available medical tubing sets are packaged with a cap in place to protect the tubing during handling. Caps for other types of connectors, including catheter injection ports, are less common, though also known in the medical capping art.

Caps commonly used to cover medical connectors include a cover that is open at one end, closed at the other end and includes a set of spiraling screw threads (for making a secure and sealed luer-type connection) over an associated bared connector, such as an injection port. The inside of the closed end can be equipped with a plastic capsule that can be ruptured when the cover is affixed to the associated connector. Rupturing of the plastic capsule releases antiseptic agents stored in the capsule, thereby applying the antiseptic agents to accessible portions of the connector.

One of the many examples of medical connectors for which such caps are used are intravascular connectors associated with a fluid pathway, such as a central line. Commonly, a fluid pathway is used to intermittently administer medications to a patient. For example, a fluid pathway, which communicates fluids with a patient's blood stream, may have one or more connectors associated therewith. Each of the fluid pathway connectors can be connected to other connectors, such as a connector associated with an IV bag. In such a situation, the medical connectors, such as luer lock connectors, are connected and disconnected at various times, and may remain disconnected for several minutes or hours. Medical connector caps are used to cover and protect the various medical connectors while the connectors are separated from one another. When the medical connectors are separated from each other, there are two connectors that can require covering by a cap. Therefore, it would be an advantage to have a single connector set that can be used to provide protection for both ends of a separated connection.

Fluid delivery into medical catheters and other devices is also well known in the art. Various fluid reservoirs including bottles, bags, and syringes are commonly attached to catheters via tubing and connectors for the purpose of delivering fluid therein. Factory pre-fill syringes have become increasingly used to limit the practice of filling syringes in healthcare facilities which may increase the risk of infections and medication/dosing errors. Regulating guidelines including USP 797 and highly publicized incidents of IV medication errors have further underscored the need for safer, low volume fluid delivery devices.

BRIEF SUMMARY

One embodiment of the present invention comprises a nested pair of protective caps having a male cap and a female cap. Each cap has threads which correspond to connectors generally used in medical apparatuses and which are separated for access thereto. Such medical apparatuses may include, but are not limited to, IV tubing sets, needleless injection sites or ports and vascular access devices. Each cap has threads that connect to a threaded end of an associated cap. As such, a pair of protective caps may be nested together to provide a pair of caps that, before separation, maintain sterile internal surfaces. These caps may subsequently be taken apart and applied to protect and seal both ends of a separated medical connection, such as medical connectors generally used in medical apparatuses, from microbial ingress or other contamination.

Each protective cap encloses an associated medical apparatus connector and prevents touch contamination that may lead to microbial contamination, colonization, and infection while the medical apparatus connectors are unattached. Further, in some embodiments, the protective caps can contain antiseptic agents that kill microorganisms such as bacteria, viruses, and fungi that may colonize and lead to body-wide infection (e.g. IV catheter related blood stream infections). In such cases, the protective cap may have an absorbent material for applying an antiseptic to an attached medical apparatus connector. The absorbent material also may provide a friction scrub while the protective cap is being connected. Such scrubbing improves microbial kill.

The "nesting" geometry of the pair of caps provides both caps as a single unit, sealed against contamination of connecting parts until the nested pair is separated. Generally, the nested pair is connected by the same thread geometries that provide for connecting to associated medical connecting apparatuses. When nested before use, the individual female and male caps are screwed together to form a seal to insure that the sterility of the internal surfaces of each cap is maintained. For this reason, the nested pair unit or device optimally does not require further sterilization before use as the unit is produced and delivered as an inherently self-sealed sterile package.

For example, the male cap from the device may be generally used to cover the end of an IV tubing set that is disconnected from an IV catheter needleless injection site. Examples of needleless injection sites, sometimes referred to as ports, hubs, and valves, include brands such as Clave (ICU Medical), SmartSite (Cardinal Health), and Q-Site (Becton Dickinson, and Co.). The female cap from the nested pair may then be used to protect the needleless injection site itself. Importantly, once the cap has been applied, the medical apparatus connector need not be re-disinfected (e.g. treated with an alcohol swab) prior to each reconnection, as it will be kept in an uncontaminated state while under the protective cap.

In an exemplary embodiment, the nested pair of pre-sterilized caps is packaged to protect against contamination by a seal covering about the junction of the two caps. Exemplary embodiments of the nested pair having a female portion and a male portion may also contain a scrubbing material in a closed end of each of the female portion and the male portion. The material can be impregnated with an antiseptic agent. The male portion screws into corresponding threads of the female portion. To assure sterility and prevent fluid loss, the abutting edges of the male and female portions form a seal impermeable to passage of fluid and microbes when tightly affixed together. The abutting edges can be over-molded or co-molded so that the abutting edges can antiseptically seal the interior surfaces of the male and female portions when the male and female portions are coupled together. Alternatively, an O-ring may be affixed about a portion containing internal threads of the male cap. Such a seal reduces or prevents evaporative loss of antiseptic and maintains the sterility of the internal surfaces of the male and female portions. A second, wrap-around seal may also or otherwise be used to provide additional protection for transport and storage. Unscrewing, to separate the two portions, breaks each such seal and prepares the female and male portions for subsequent connection to separated medical connectors. The female portion can then be secured to a male medical connector to protect and seal the male medical connector. Similarly, the male portion can be secured to a female medical connector to protect and seal the female medical connector. As the female portion is secured onto the male medical connector, the scrubbing material disposed in the female portion scrubs the opening edges of the male connector. Likewise, as the male portion is secured onto the female medical connector, the scrubbing material disposed in the male portion scrubs the leading edges of those parts of the female connector that are received within the closed end of the male portion. This, in addition to prevention of contamination, thereby eliminates need for routine swabbing (e.g. by alcohol).

Other exemplary embodiments provide nested and sealed male and female portions and a fluid reservoir coupled to one of the caps. The fluid reservoir can be adapted to communicate fluid through a channel in the associated cap to a separated medical connector. The fluid within the fluid reservoir can be a medicine or antiseptic agent. In one embodiment, the fluid reservoir is adapted to diffuse the fluid through the associated cap over time. In an alternative embodiment, the fluid reservoir is adapted to dispense the fluid from the fluid reservoir into a fluid pathway. As used herein, a fluid pathway can include, but is not limited to, a central line, a PICC line, a feeding tube, a drain tube, or nearly any type of catheter, including urinary, pulmonary artery, or cardiac catheters. In this embodiment, the fluid reservoir can comprise an elastomeric bulb, a collapsible bulb, a dual-barrel chamber, or a syringe-type barrel-plunger system. The fluid reservoir can be used to administer medicine to a patient through a fluid pathway, or provide an antiseptic to the targeted fluid pathway to maintain catheter patency, or to reduce or eliminate the existence of microbes within the fluid pathway. For example, a specific amount of fluid, such as heparinized saline or other anticlotting medication, could be primed into a central line to maintain catheter patency.

Additional features and advantages of the present invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

FIG. 1 is a side elevation view of an attached pair of medical caps made according to the instant invention;

FIG. 1A is a first end perspective view of the caps of FIG. 1;

FIG. 1B is a second end perspective view of the caps of FIG. 1;

FIG. 2 is an exploded perspective view of the medical caps of FIG. 1;

FIG. 3 is a perspective view of a single cap portion of the attached pair seen in FIG. 2, with internal threads seen therein;

FIG. 4 is a perspective view of the cap seen in FIG. 3 with an associated medical connector about to be connected thereto;

FIG. 5 is a perspective view of a cap, which is complimentary to the cap of FIG. 3, and a luer lock connector to which the complimentary cap may be affixed;

FIG. 10 is an exploded side elevation view of a pair of complimentary caps, similar to the caps seen in FIG. 1, but having a tube portion which is sized and shaped to fit through a hole in the female portion of the nested pair, the tube portion having a frangible fluid reservoir therein;

FIG. 11 is a side elevation view of the complimentary caps seen in FIG. 10 interconnected with the tube portion;

FIG. 12 is a side elevation view of a pair of complimentary caps, similar to caps seen in FIG. 9D, with a second absorbent pad disposed therein;

DETAILED DESCRIPTION

Figure 7:
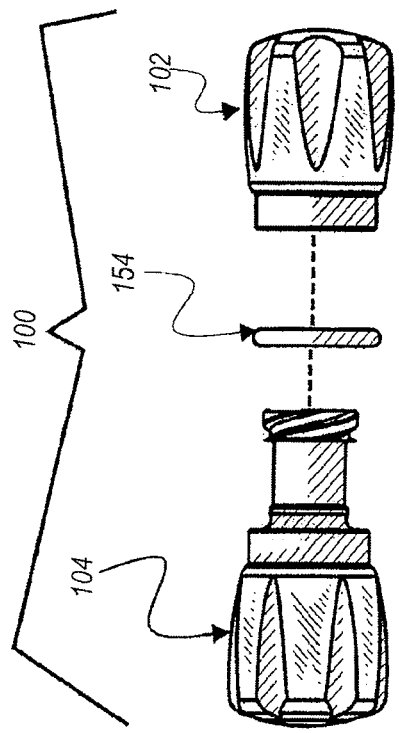
FIG. 7 is an exploded view of the cap assembly seen in FIG. 6.

The present invention relates generally to a pair of nestable caps, each of the caps being sized and shaped to provide a protective union about a separated medical connector. The pair comprises a male cap and a female cap, each of which is configured to be adjoined to a complimentary cap to form a nested pair. The nested pair is sealed until separated for use, thereby maintaining sterility of the internal surfaces of the nested pair. One of the caps may have a fluid chamber joined thereto filled with medicine or antiseptic. The cap associated with the fluid chamber can have a channel extending therethrough to provide fluid communication between the fluid chamber and a fluid pathway. The fluid chamber can be adapted to diffuse the fluid into the fluid pathway over time, or the fluid chamber can be adapted to dispense the fluid out of the fluid chamber.

Seen in FIGS. 1-1B, is a unit or assembly 100 of a pair of separable caps 102 and 104 securely, but releasably affixed one to the other across a common interface 106. To serve a meaningful purpose, internal parts and surfaces of assembly 100 must be sterile and, perhaps more important, be able to reduce, prevent, or eliminate contamination of a connector with which each cap becomes associated.

Caps 102 and 104 are seen apart in FIG. 2, wherein cap 104 is seen to have an insertable or male section 108. Section 108 has an elongated portion 110 that ends at an exteriorly disposed threaded segment 112. Threaded segment 112 comprises threads 114 that are sized and shaped to be inserted and joined by threading into cap 102.

Cap 102, which is better seen in FIG. 3, has a closed, hollow interior 116 which opens outwardly at a proximal end 118 to expose an interiorly disposed threaded segment 120. Threads 122 are of a size and pitch to complimentarily engage threads 114 for a screw or push on tight fit with cap 104.

As illustrated in FIG. 4, cap 102 has an interior surface 124, an opening edge 126 and an exterior surface 128, opening edge 126 being a common link between interior surface 124 and exterior surface 128. Further, threads 122 also have a size and pitch to engage a threadable segment 130 of a female connector, such as for example, female luer connector 132. Such connectors are generally and commonly used as catheter and other fluid tight protective connectors in medical applications. As seen in FIG. 4, cap 102 provides a protective cover for connector 132 when encased about connector 132 (displaced in direction of arrow 134) where upon threadable segment 130 engages and is drawn into a secure, but releasable connection with threads 122 of cap 102.

Likewise, as seen in FIG. 5, threads 114 of cap 104 are of a size and pitch to engage threads 138 of a male luer-lock connector 136. Note that cap 104 has a medially disposed, elongated hole 140, into which a frustoconical cone shaped luer 142 of connector 136 may be facilely and securely inserted when cap 104 is displaced in direction of arrow 144 to engage connector 136.

Cap 104 also has a surface 146 which continues through to a circular edge 148. Further, distally displaced from circular edge 148, surface 146 abruptly ends at a circular ring shaped edge 150, which is therefrom joined to an outside surface 152. It may be noted that opening edge 126 (see FIG. 4) and ring shaped edge 150 combine to form common interface 106 (see FIG. 1) when cap 102 is affixed to cap 104 to construct assembly 100. It should also be noted that surfaces of assembly 100, which contact internal surfaces of a connector, such as connector 132 or connector 136, should be sufficiently sterile to not contaminate the inner surfaces thereof.

For this reason, internal portions and associated edges of caps 102 and 104 should be pre-sterilized and so maintained until use. Caps 102 and 104 may be injection molded using polypropylene or other material that can be sterilized and which is impervious to contaminating agents while cap 102 is fully nested with cap 104, before being opened for use. Caps 102 and 104 can also be impregnated or coated with an antimicrobial substance. As an example, each cap 102 and cap 104 may be individually sterilized by ethylene oxide (ETO) before final assembly and aseptically paired, or assembly 100 may be finally consolidated as a single unit and then sterilized, such as by radiation (e.g. gamma). Even so, assembly 100 should be kept intact until time for use, with internal surfaces of nested parts 102 and 104 remaining clean and sterile until assembly 100 is opened for use.

Figure 7B:
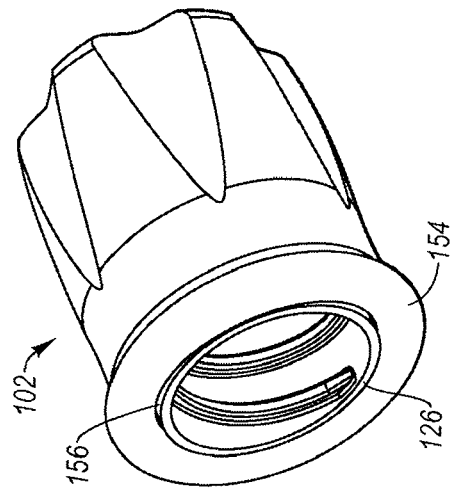
FIG. 7B is an end perspective view of the other cap seen in FIG. 7 with a sealing mechanism disposed thereon.
Figure 6:
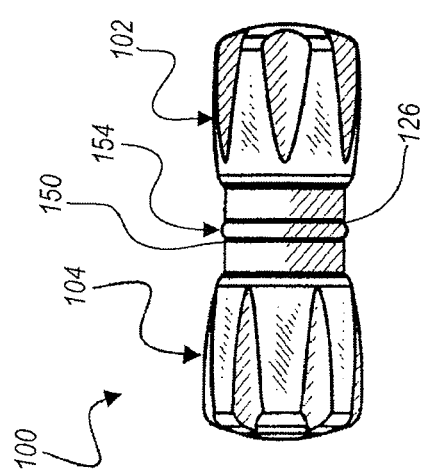
FIG. 6 is a side elevation view of an attached pair of medical caps, similar to the caps seen in FIG. 1, but having an "O" ring disposed about connecting edges of the caps.
Figure 7A:
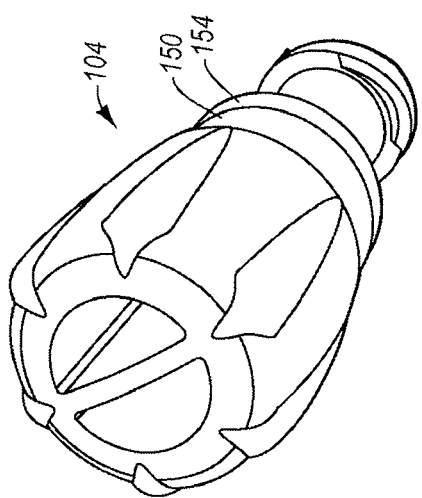
FIG. 7A is an end perspective view of one of the caps seen in FIG. 7 with a sealing mechanism disposed thereon.

Reference is now made to FIGS. 6 through 7B, wherein a seal, such as an "O" ring, is disposed between surfaces 126 and 150 to provide yet another barrier against internal surface contamination of caps 102 and 104. As seen in FIG. 6, an "O" ring 154 is disposed between surfaces 126 and 150 to provide a seal thereby. While "O" ring 154 can be displaced from caps 102 and 104 as illustrated in FIG. 7, it is anticipated that "O" ring 154 can be adapted to remain affixed to one of caps 102 and 104. For example, as illustrated in FIG. 7A, "O" ring 154 can remain positioned adjacent surface 150 on cap 104 when caps 102 and 104 are disconnected from one another, rather than being separated when cap 104 is displaced from cap 102, as seen in FIG. 7.

Alternatively, "O" ring 154 can be associated with cap 102, as seen in FIG. 7B. In particular, opening edge 126 of cap 102 can have an annular groove 156 for receiving "O" ring 154 therein. Annular groove 156 can be sized and shaped such that "O" ring 154 sealingly engages cap 104 or a medical connector when cap 102 is coupled thereto. It will be appreciated that annular groove 156 can be disposed in opening edge 126 toward the exterior of cap 102 as illustrated in FIG. 7B, or annular groove 126 can be disposed in opening edge 126 towards the interior of cap 102. In some exemplary embodiments, opening edge 126 of cap 102 does not have annular groove 126 therein. In such embodiments, "O" ring 154 can be mounted directly to opening edge 126. "O" ring 154 can be mounted on or to caps 102 or 104 in any suitable manner, including with the use of an adhesive, such as glue, a mechanical fastener, or a friction fitting.

While the seal between caps 102 and 104 has been described as being an "O" ring mounted on one of caps 102 or 104, it will be appreciated that other seals are contemplated within the scope of the present invention. For example, each of caps 102 and 104 can have an "O" ring mounted thereon. In such a configuration, the two "O" rings abut each other when caps 102 and 104 are coupled together, thereby forming a seal to antiseptically partition the internal and external surfaces of caps 102 and 104. Alternatively, one or both of caps 102 and 104 can be formed with a lip, bump, or groove that provides a sealing function when caps 102 and 104 are coupled to each other or to separated medical connectors. In one exemplary embodiment, one of caps 102 and 104 has a ridge extending around its interfacing surface, and the other cap has a corresponding groove in its interfacing surface into which the ridge is received to create the seal. In yet another exemplary embodiment, one or both of caps 102 and 104 can be overmolded or comolded using any known and suitable overmolding or comolding process. For example, one or both of caps 102 and 104, and associated surfaces 126 and 150, can be overmolded or comolded. Thus, caps 102 and 104 can be formed of a polymer, and surfaces 126 and 150 can be formed of a softer polymer that is comolded or overmolded to the rest of caps 102 or 104. Surfaces 126 and 150, formed of the softer polymer, are thus able to be compressed or deformed sufficiently to create an impermeable seal when caps 102 and 104 are coupled together or coupled to separated medical connectors.

As noted elsewhere herein, a sealing mechanism, as described herein, can be used to limit or prevent evaporation or loss of an antiseptic agent disposed within caps 102 and 104 when caps 102 and 104 are coupled together. Additionally, a sealing mechanism, as described herein, can also limit or prevent evaporation or loss of an antiseptic agent disposed within caps 102 and 104 when caps 102 and 104 are coupled to separated medical connectors. Further, a sealing mechanism, as described herein, can also limit or prevent microbial ingress within caps 102 and 104 when coupled to each other, or within caps 102 and 104 when caps 102 and 104 are individually coupled to separated medical connectors. Moreover, a sealing mechanism, as described herein, can be adapted to maintain an antiseptic agent within caps 102 and 104 when caps 102 and 104 are either coupled to one another or to separated medical connectors for a predetermined amount of time. Thus, the seal may be adapted to limit or prevent microbial ingress while also partially or completely preventing evaporation of an antiseptic agent disposed within caps 102 and 104 when caps 102 and 104 are coupled together or when caps 102 and 104 are coupled to separated medical connectors. Similarly, the seal may be adapted to limit or prevent microbial ingress while not preventing evaporation of an antiseptic agent disposed within caps 102 and 104. In yet other embodiments of the invention, no seal is provided between caps 102 and 104 when coupled together or between caps 102 and 104 when coupled to separated medical connectors.

Figure 8B:
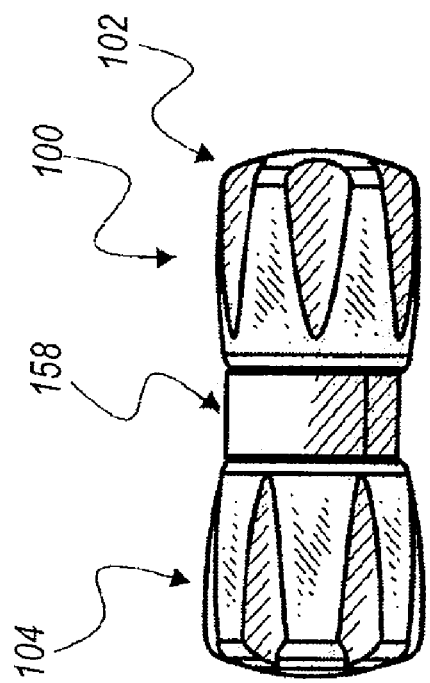
FIG. 8B is a side elevation view of the interconnected cap assembly seen in FIG. 8A with the planar or foil seal fully in place.
Figure 8A:
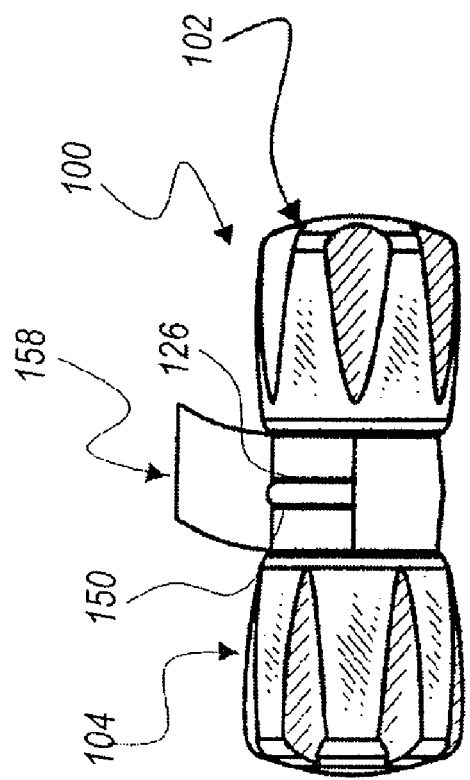
FIG. 8A is a side elevation view of the interconnected cap assembly seen in FIG. 6 with a planar or foil seal partially displaced about connecting edges of the cap assembly.

Further safety in sealing against internal surface contamination may be provided by a sealing tape, such as tape 158 seen in FIG. 8A. Tape 158 is disposed to fully cover exposed edges of surfaces 126 and 150. Tape 158 may, for example, be of an impervious pliable material, such as a metallized-surface mylar. As seen in FIG. 8B, tape 158 is wrapped about surfaces 126 and 150 to provide a secure seal. It is preferred that tape 158 frangibly divides when cap 102 is separated from cap 104 to facilitate separation of caps 102 and 104 and provide a visible indication that the seal is broken. Thus tape 158 provides both a seal to prevent microbial ingress and a mechanism for maintaining the secure connection between caps 102 and 104 prior to use. It will be appreciated, however, that any suitable sealing mechanism can be used to maintain the secure connection between caps 102 and 104 prior to use. For example, any sealing mechanism can be used that securely and selectively couples caps 102 and 104 together, requires deliberate action to break the seal, and provides a visual indication of whether the seal has been broken. By way of example and not limitation, a suitable sealing mechanism may include a heat stake, a frictional seal, a barbed seal, a ratchet seal, and the like.

Figure 9C:
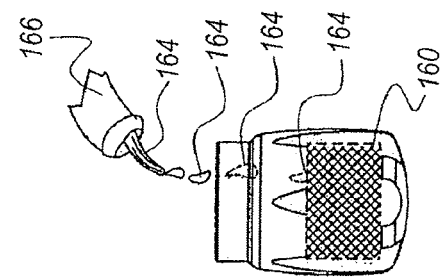
FIG. 9C is a side elevation view of the cap portion and pad as seen in FIG. 9B with a quantity of antiseptic material being dispensed into the cap and pad.

When capping disconnected medical connectors, it is prudent to do more than just cover those connectors with caps. For this reason, an absorbent pad, such as pad 160, seen in FIG. 9A, may be displaced into cap 102 as indicated by arrow 162. Pad 160 is seen disposed in cap 102 in FIG. 9B. An antiseptic 164 can also be disposed within cap 102 as illustrated in FIG. 9C. Antiseptic 164 can be in liquid or solid form. For example, alcohol or another stable liquid antiseptic may be added from a container 166 to saturate pad 160 to a predetermined level. Note that once assembly 100 is fully assembled, pad 160 will substantially remain at the predetermined saturation level due to the exterior seals provided for assembly 100 as described herein. Alternatively, or additionally, pad 160 may be impregnated with a dry antiseptic, such as chlorhexidine gluconate.

Figure 9E:
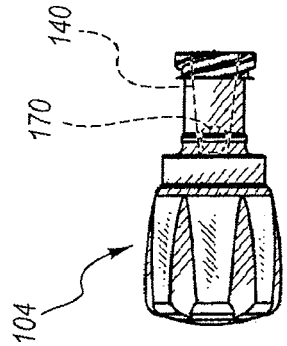
FIG. 9E is a side elevation view of the cap portion which is seen in FIG. 5 and an absorbent pad disposed there above.
Figure 9B:
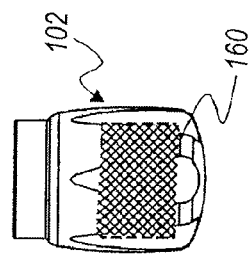
FIG. 9B is a side elevation view of the cap portion and pad seen in FIG. 9A with the absorbent pad disposed within the cap portion.
Figure 9A:
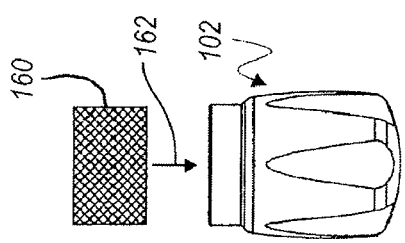
FIG. 9A is a side elevation view of the cap portion which is seen in FIG. 3 and an absorbent pad being disposed there above.
Figure 9D:
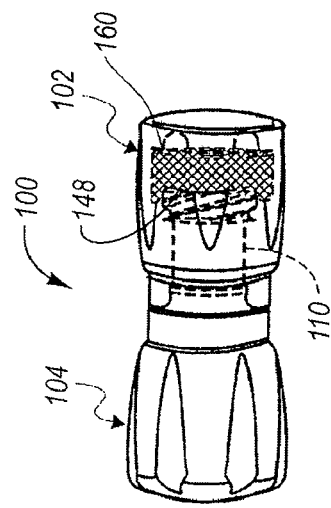
FIG. 9D is a horizontal perspective view of the cap portion containing the pad as seen in FIGS. 9B and 9C affixed to an associated complimentary cap.

Further note that once cap 104 is securely affixed to cap 102, as seen in FIG. 9D, pad 160 is disposed to contact at least circular edge 148 (see also FIG. 5). (In FIG. 9D, parts of cap 104 which are internal to assembly 100 are seen with hidden or dashed lines.) Such contact provides a wiping action preferred to make contact with a surface before contact is made with an associated connector. Note also that residual antiseptic on associated internal surfaces of cap 104 may be transferred to related parts of the associated connector for cleaning and/or disinfecting purposes.

Pad 160 can be formed of a deformable, resilient material such that when cap 104 is coupled to cap 102, elongated portion 110 can compress pad 160 within cap 102, as illustrated in FIG. 9D. Further, pad 160 can expand to its original shape when cap 104 is removed from cap 102. Similarly, pad 160 can be compressed within cap 102 when cap 102 is coupled to a medical connector, such as medical connector 132. More specifically, during the connection of cap 102 to a medical connector, cap 102 and pad 160 rotate relative to an opening edge of the medical connector, thereby drawing the medical connector into cap 102. The rotation of cap 102 causes pad 160 to wipe or scrub the opening edge of the medical connector. Pad 160 and any antiseptic disposed within cap 102 can thus cleanse and disinfect the opening edges of the medical connector. Pad 160 can also be formed such that when a medical connector is coupled to cap 102, pad 160 is deformed such that pad 160 extends around the opening edges and/or threads of the medical connector. For example, pad 160 can be formed such that as cap 102 is twisted onto medical connector 132, pad 160 deforms around threads 130 and/or the opening edges of medical connector 132, thereby scrubbing threads 130 and/or the opening edge of medical connector 132.

Pad 160 can also provide additional functionality when a liquid antiseptic is disposed within cap 102. In particular, pad 160 acts as a sponge to absorb or release the liquid antiseptic within cap 104. More specifically, when pad 160 is compressed by elongate portion 110 of cap 104 (FIG. 9D; see also elongate portion 268 compressing pad 160 in FIG. 14) or the opening edges of a medical connector coupled to cap 102, pad 160 releases the antiseptic so that the antiseptic can be transferred to elongate portion 110 or the opening edges of the medical connector. Conversely, when cap 102 or a medical connector is disconnected from cap 102, pad 160 expands and absorbs excess antiseptic so that the antiseptic does not drip or spill out of cap 102.

Similar to pad 160 and antiseptic 164 disposed within cap 102, cap 104 may also have a pad and/or an antiseptic disposed therein. For example, as illustrated in FIG. 9E, a pad 170 may be disposed within elongate hole 140 of cap 104. An vantiseptic can also be disposed within cap 104 in a manner similar to antiseptic 164 in cap 102. Antiseptic can be in liquid or solid form. For example, alcohol or another stable liquid antiseptic may be added from a container to saturate pad 170 to a predetermined level. Alternatively, or additionally, pad 170 may be impregnated with a dry antiseptic, such as chlorhexidine gluconate. Once assembly 100 is fully assembled, an antiseptically saturated pad 170 disposed within cap 104 will substantially remain at the predetermined saturation level due to the exterior seals for assembly 100 as described above. Once caps 102 and 104 are disconnected from each other and connected to individual medical connectors, pad 170 disposed within cap 104 may scrub related parts of the associated connector for cleaning and/or disinfecting purposes. It will be appreciated, however, that in some embodiments, pad 170 may not contact a medical connector coupled to cap 104. Additionally, the antiseptic disposed within cap 104 may be transferred to the related parts of the associated medical connector for cleaning and/or disinfecting purposes.

Under some conditions, it may be preferable to retain an antiseptic solution within a container prior to separating the nested caps. Reference is now made to FIGS. 10-11 wherein an assembly 200 is seen to comprise a first cap 204, a second cap 202 and an antiseptic containing vessel 206.

As seen in FIG. 10, geometric features of cap 202 are similar to features of cap 102 except for a through hole 208 in end 210, providing access into cap 202. Rather than an absorbent pad 160 (see FIG. 9D), an absorbent pad 212 is resident at an open end 214 of a hollow pliable tube 216. Tube 216 is closed at an opposite end 218. Also, retained in tube 216 by pad 212 and closed end 218 is a frangible capsule 220 which is filled with a predetermined amount of antiseptic solution.

Note that tube 216 is sized, shaped, and of a material to fill and be securely and sealingly affixed to cap 202 to provide a seal about hole 208. A commercially available frangible reservoir tube such as the ChlorPrep Sepp Applicator provided by Enturia may be used for vessel 206.

As seen in FIG. 11, tube 216 is displaced into hole 208 to be adhesively affixed thereat. Resultingly, vessel 206 becomes an integral part of assembly 200. Prior to separating cap 204 from cap 202, capsule 220 is manually crushed to cause fluid 222 contained therein to be released into the void of parts of assembly 200 through pad 212.

As discussed herein, it is common for a cap, such as caps 104 and 204 to be used to protect a male luer connector. In such a case, a cap 204 seen in FIG. 12 is seen to contain a hollow frustoconically shaped internal connector surface 224. To further cleanse a male luer connector inserted therein, a second antiseptic filled pad 226 is disposed at the deepest point thereof for contact with the end of the male connector.

Figure 13:
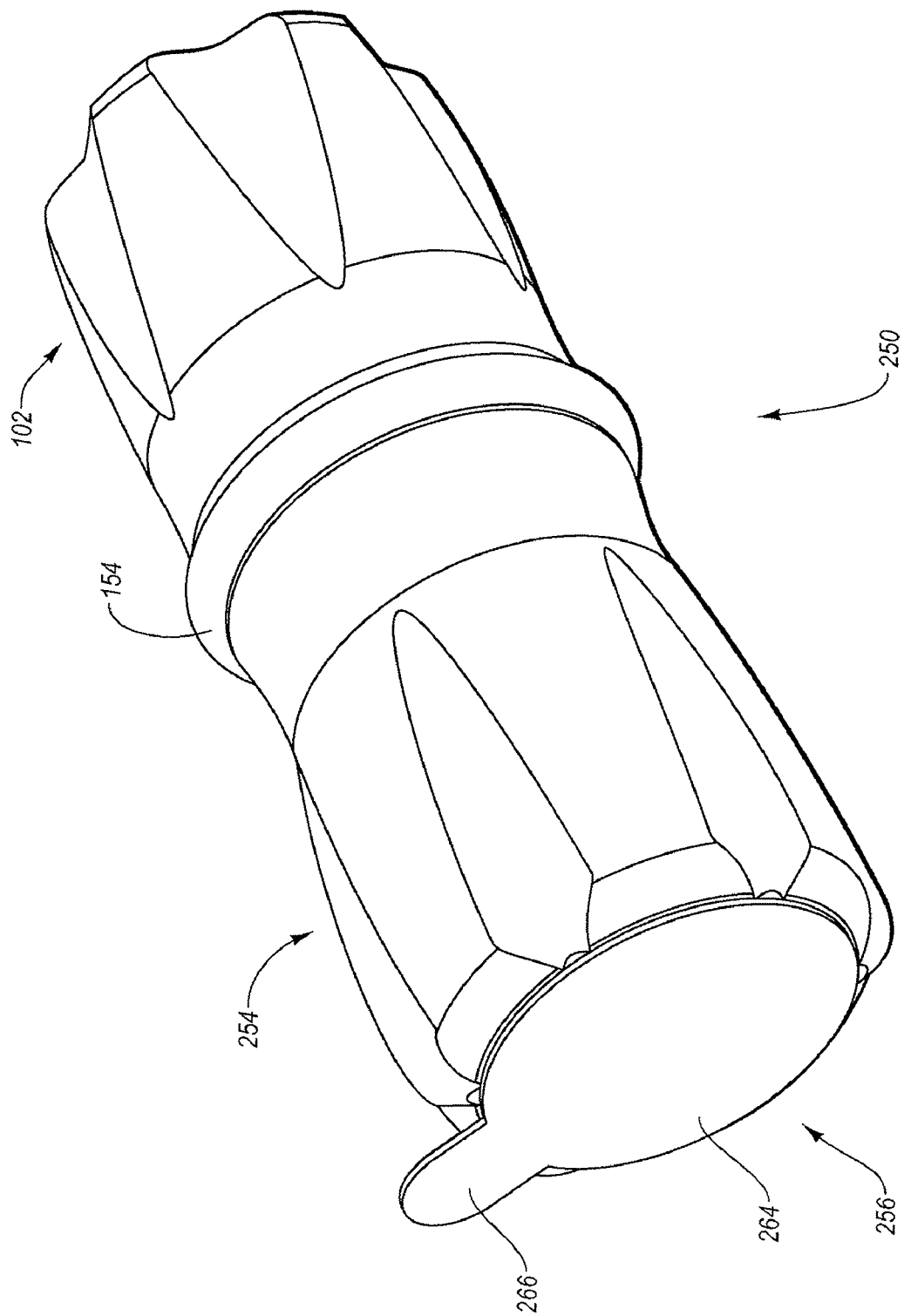
FIG. 13 a perspective view of a pair of complimentary caps, similar to the caps seen in FIG. 1, but having an additional scrubbing device disposed in an end of one of the caps.
Figure 14:
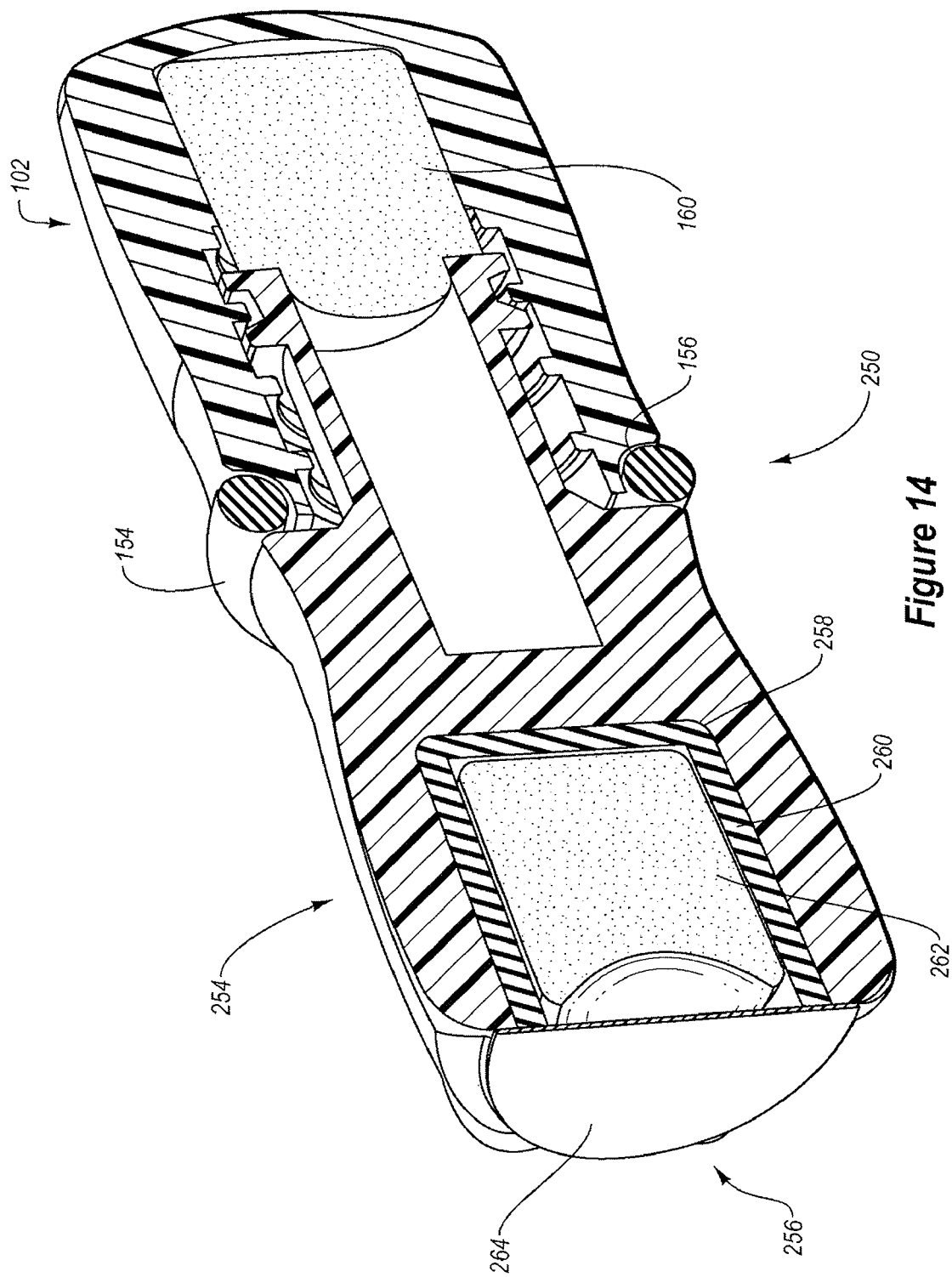
FIG. 14 is a cross-sectional perspective view of the pair of caps of FIG. 13.

With attention to FIGS. 13 and 14, another exemplary embodiment of a nestable pair of caps 250 is illustrated having a female cap 102 and a male cap 254, similar to the caps previously described herein. Disposed between caps 102 and 254 can be a sealing mechanism 154 as described herein. Additionally, one or both of caps 102 and 254 can have a scrubbing chamber 256 disposed within an end thereof. Scrubbing chamber 256 can be adapted to clean, disinfect, and remove particulate from a medical connector prior to connecting the medical connector to another medical connector or to one of caps 102 and 254.

In the illustrated embodiment, scrubbing chamber 256 is disposed within cap 254, however, it will be appreciated that scrubbing chamber 256 can be disposed within the end of cap 102. Scrubbing chamber 256 comprises a cavity 258 within the end of cap 254. Positioned within cavity 258 is a liner 260 and a pad 262 disposed within liner 260. Liner 260 can be removably secured within cavity 258 such that liner 260 can be securely held in place during use of cap 254 and/or scrubbing chamber 256, and removed after use of scrubbing chamber 256. Liner 260 can also be adapted to be removed from cavity 258 prior to use of scrubbing chamber 256, such that scrubbing chamber 256 can be used independently of caps 102 or 254. Scrubbing chamber 256 may be used to remove potentially hazardous material and particulates, such as blood, body fluids, drug particulate, and the like, from off of a medical connector prior to the medical connector being secured to another medical connector or to one of caps 102 or 254. After scrubbing chamber 256 has been used, the contents of scrubbing chamber 256, including liner 260, pad 262, and any particulate removed from the medical connector, can be removed from cap 254 and discarded so that the hazardous material does not remain near the medical connector when the cap is coupled thereto.

As noted above, disposed within liner 260 is pad 262. Similar to pad 160 described herein, pad 262 can be formed of a deformable material capable of deforming around the opening and threads of a medical connector. Additionally, or alternatively, pad 262 can be formed such that the edges of pad 262 extend closer to the opening of scrubbing chamber 256 than the central portion of pad 262, as illustrated in FIG. 14. The extending edges of pad 262 can be adapted to wrap at least partially around the edges of a medical connector so as to enable cleaning, disinfecting, or removal of particulate from outer surfaces and/or threads of a medical connector. Pad 262 can also be formed of an abrasive material that can break up hardened materials that have collected on a medical connector. Additionally, pad 262 can be formed of a material that can be impregnated or saturated with an antiseptic agent, such as alcohol or -chlorhexidine gluconate.

Scrubbing chamber 256 can also include a removable cover 264 for enclosing liner 260, pad 262, and any antiseptic agent within cavity 258. As illustrated in FIG. 14, cover 264 extends across the opening to cavity 258 and is secured to cap 254. Cover 264 can be secured to cap 254 is any manner that sealingly maintains the contents of cavity 258 therein and that allows for ready removal of cover 264 when scrubbing chamber 256 is to be used. Cover 264 can be formed of any suitable material, such as foil, plastic, and the like. Additionally, cover 264 can also include a tab 266 that facilitates quick and convenient removal of cover 264 when scrubbing chamber 256 is to be used.

Figure 15:
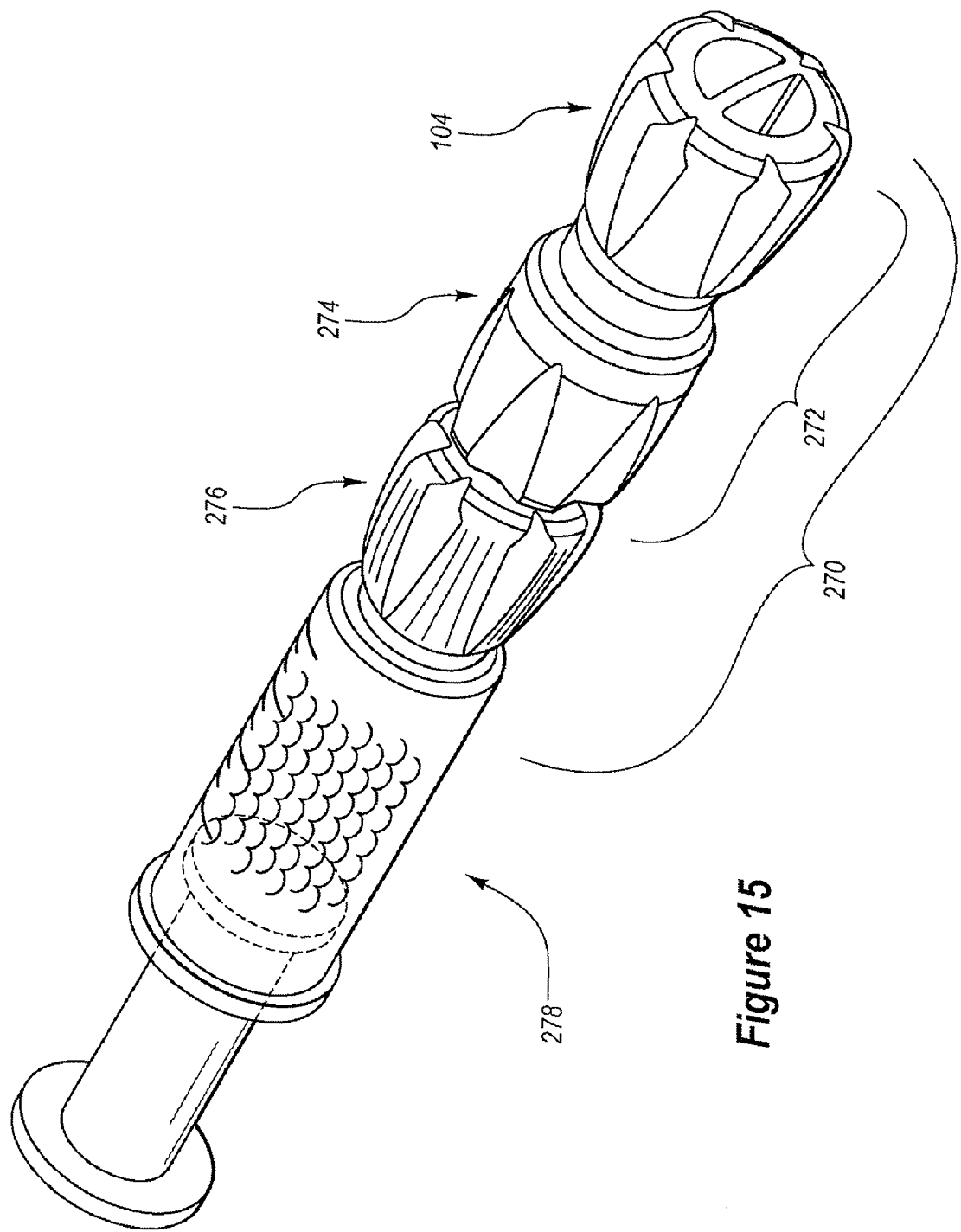
FIG. 15 is a perspective view of an attached pair of medical caps, similar to the caps seen in FIG. 1, but with one of the caps having a secondary cap portion extending from an end thereof such that the secondary cap portion can be used to cap a pre-filled syringe.

In the exemplary embodiment of the present invention illustrated in FIG. 15, a cap assembly 270 including a nestable pair of caps 272, having a female cap 274 and a male cap 104, is provided. Male cap 104 and female cap 274 are similar to the other caps described herein. Specifically, the caps nestably couple together to protect the sterility of their interior surfaces and can be separated and coupled to separated medical connectors to protect the sterility of the separated connectors. Additionally, one of the caps can have a secondary cap portion disposed on an end thereof. For example, in the illustrated embodiment, one end of female cap 274 is formed to receive a portion of and be coupled to male cap 104 or a male medical connector as described herein. Additionally, the other end of female cap 274 is formed with a secondary cap portion 276 such that secondary cap portion 276 can be selectively and securely coupled to a prefilled syringe 278, for example. It will be appreciated that secondary cap portion 276 could also be formed on an end of cap 104. Secondary cap portion 276 can be formed to securely and sealingly couple to a fluid coupling interface portion of syringe 278 to as to protect the sterility of the fluid coupling interface portion of syringe 278. In this configuration, nestable pair of caps 272 can be coupled to prefilled syringe 278 prior to use of prefilled syringe 278, while maintaining the sterility of the fluid coupling interface portion of syringe 278. In one embodiment of cap assembly 270, secondary cap portion 276 can be selectively disconnected from cap 274 either before or after use of syringe 278. Likewise, secondary cap portion 276 could be disconnected from pair of caps 272 so that pair of caps 272 and syringe 276 can be used independently from one another.

Coupling pair of caps 272 to secondary cap portion 276 and syringe 278 in the manner described herein provides the convenience of having a pair of caps 272 readily available after a pre-filled syringe is used to dispense a fluid into a fluid pathway. In use, for example, a medical professional could separate a set of medical connectors in order to administer the fluid within syringe 278 to one or both of the fluid pathways associated with the medical connectors. In order to use syringe 278, cap 276 is removed from syringe 278. With cap 276 removed, syringe 278 can be coupled to one or both of the separated medical connectors and the fluid within syringe 278 can be dispensed into the fluid pathway. After use of syringe 278 is complete, pair of caps 272 can be separated into individual caps 274 and 104, which can then be coupled to the separated medical connectors in the same manner as described herein with reference to caps 102 and 104, for example.

With attention to FIGS. 16-29, additional exemplary embodiments of caps according to the present invention will be described. While the various aspects, features, and characteristics of the exemplary embodiments illustrated in FIGS. 16-29 will be described with specific reference to a female type cap, similar to cap 102, it will be appreciated that the same aspects, features, and characteristics may be applied to or incorporated within a male type cap, similar to cap 104. Furthermore, it will be appreciated that the female type caps described with reference to FIGS. 16-29 can be coupled to a male type cap in a manner similar to that described above with reference to caps 102 and 104 in order to create a nested pair of caps. Alternatively, the embodiments described with reference to FIGS. 16-29, whether in a male or female type cap, can be formed and/or employed without having to be nested or otherwise associated with a complimentary cap.

Figure 16:
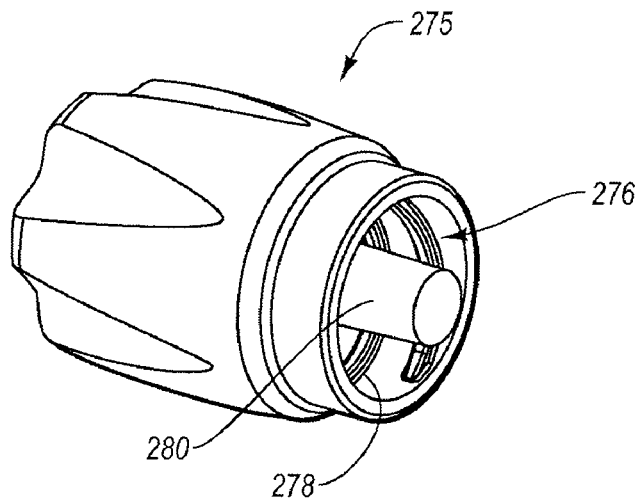
FIG. 16 is a perspective view of a single medical cap, similar to the cap seen in FIG. 3, but having a post disposed therein to sealingly engage an interior surface of a medical connector when coupled thereto.
Figure 17:
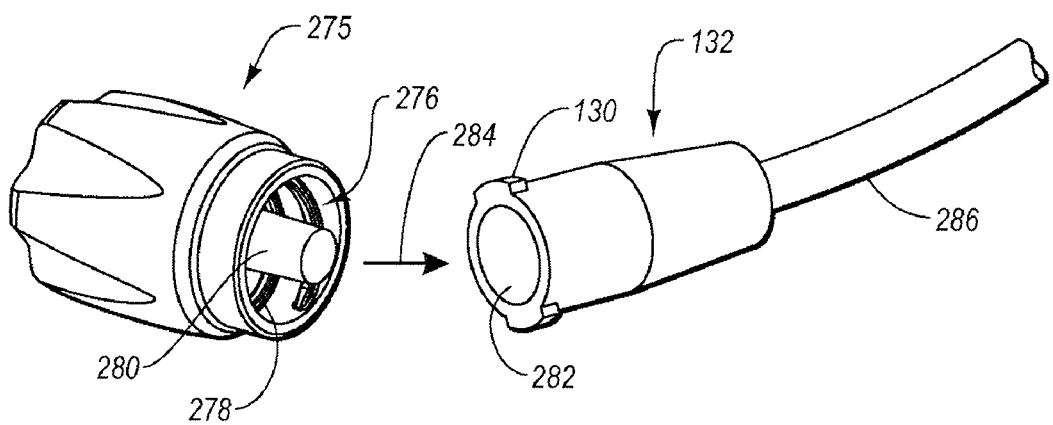
FIG. 17 is a perspective view of the cap seen in FIG. 16 with an associated medical connector about to be connected thereto.

With specific reference to FIGS. 16 and 17, a cap 275 in accordance with an exemplary embodiment of the present invention is illustrated. Cap 275 has an interior portion 276. Disposed on at least one surface of interior portion 276 are threads 278, which are of a size and pitch to complimentarily engage threads of another cap, such as cap 104, or a medical connector to facilitate coupling thereto as discussed herein. Cap 275 further includes a frustoconical cone shaped post 280 positioned in the center of interior portion 276. Similar to the caps describe elsewhere herein, cap 275 can have a pad, saturated or impregnated with an antiseptic agent, disposed within interior portion 276 and about post 280 to cleanse portions of a medical connector coupled thereto.

As seen in FIG. 17, cap 275 provides a protective cover for connector 132 when encased about connector 132 (displaced in direction of arrow 284) where upon threadable segment 130 engages and is drawn into a secure, but releasable connection with threads 278 of cap 275. Post 280 is sized and shaped to be received within conduit 282 of connector 132 when cap 275 is secured on connector 132. Post 280 is further sized and configured to sealingly engage the outer wall of conduit 282 to prevent fluid within fluid pathway 286 from leaking out of connector 132 when cap 275 is secured thereon. Post 280 is also sized and shaped to fit within a medially disposed, elongated hole of a male type cap when cap 275 is coupled thereto. For example, post 280 is adapted to fit within hole 140 of cap 104 (FIG. 5) when cap 275 is coupled to cap 104.

Figure 18:
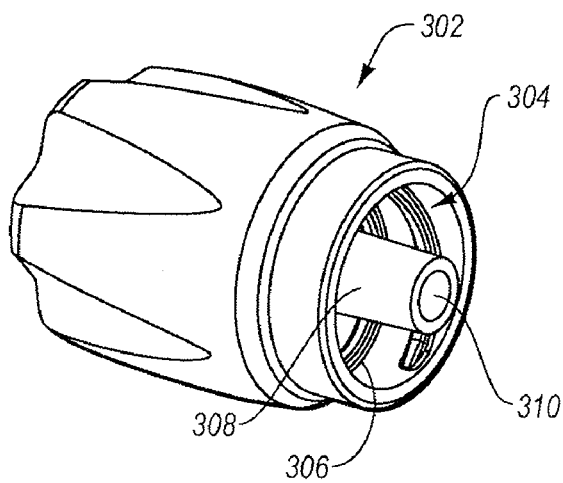
FIG. 18 is a perspective view of a single medical cap, similar to the cap seen in FIG. 16, but having an orifice within the post to receive a spike of a medical connector when coupled thereto.
Figure 19:
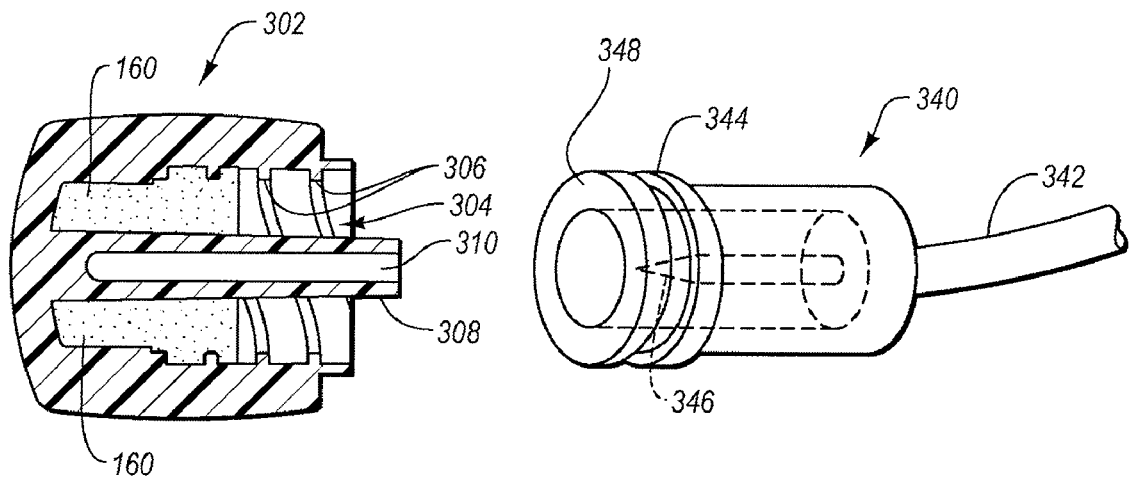
FIG. 19 is a cross-sectional view of the cap seen in FIG. 18 with an associated medical connector about to be connected thereto.
Figure 20:
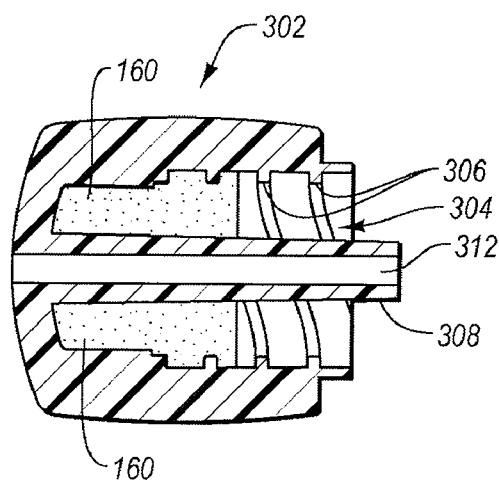
FIG. 20 is a cross-sectional view of a single medical cap, similar to the caps seen in FIG. 16-19, but having a channel extending entirely through the post to communicate fluid through the cap when the cap is coupled to a separated medical connector.

FIGS. 18-20 illustrate exemplary embodiments of a cap 302, which is similar to cap 275. In particular, cap 302 has an interior portion 304 with threads 306 disposed on at least one surface thereof. Threads 306 are of a size and pitch to complimentarily engage threads of another cap, such as cap 104, or a medical connector, such as connector 340, to facilitate coupling thereto as discussed herein. Furthermore, cap 302 includes a frustoconical cone shaped post 308 positioned in the center of interior portion 304. Similar to post 280, post 308 is sized and shaped to be received within and sealingly engage a conduit of connector 340 when cap 302 is secured on connector 340 to prevent fluid within a fluid pathway from leaking out of the connection between connector 340 and cap 302. Additionally, post 308 is also sized and shaped to fit within a medially disposed, elongated hole of a male type cap when cap 302 is coupled thereto. For example, post 308 is adapted to fit within hole 140 of cap 104 (FIG. 5) when cap 302 is coupled to cap 104.

Additionally, as illustrated in FIG. 19, disposed within interior portion 304 and about post 308 is a pad 160, which can be saturated or impregnated with an antiseptic agent, as discussed herein. With either connector 340 or a male type cap, such as cap 104, connected to cap 302, pad 160 is disposed to contact at least a portion of connector 340 or cap 140 in a manner similar to that described above with reference to FIG. 9D. More specifically, pas 160 is disposed to contact at least the opening edge 348 of connector 340 or circular edge 148 of cap 104 to cleanse at least opening edge 348 of connector 340 and circular edge 148, as discussed herein.

While post 308 includes many of the same characteristics of post 280, post 308 further includes an orifice or channel. More specifically, as illustrated in FIGS. 18 and 19, post 308 includes orifice 310 that extends from an end of post 308 at least partially through the interior thereof. Orifice 310 is sized and shaped to receive a spike 346 of a medical connector 340, such as a Clave® connector, when cap 302 is coupled to medical connector 340. Alternatively, post 308 can include a channel 312, as illustrated in FIG. 20, which extends entirely through post 308. Channel 312 can receive a spike 346 of a medical connector 340. Additionally, channel 312 can provide a fluid passageway through cap 302 for purposes described elsewhere herein.

Attention is now directed to FIGS. 21-29, which illustrate various exemplary cap assembly embodiments according to the present invention. Each of the example embodiments includes cap 302 with channel 312 extending therethrough, as described above, and a fluid reservoir joined thereto. The cap assemblies of the present invention can be adapted to communicate fluid from the fluid reservoir, through cap 302, to a fluid pathway associated with a patient. Such communication of fluid can be to provide medication to a patient, disinfect the fluid pathway, or maintain catheter patency.

As noted, the various features and characteristics of cap 302 and the cap assemblies described below can be incorporated into a male type cap, such as cap 104. Additionally, it will be appreciated that the cap assemblies described below, which incorporate cap 302, can be coupled to a male type cap, such as cap 104, to create a pair of sterile, nested caps as described above with respect to caps 102 and 104.

Figure 21:
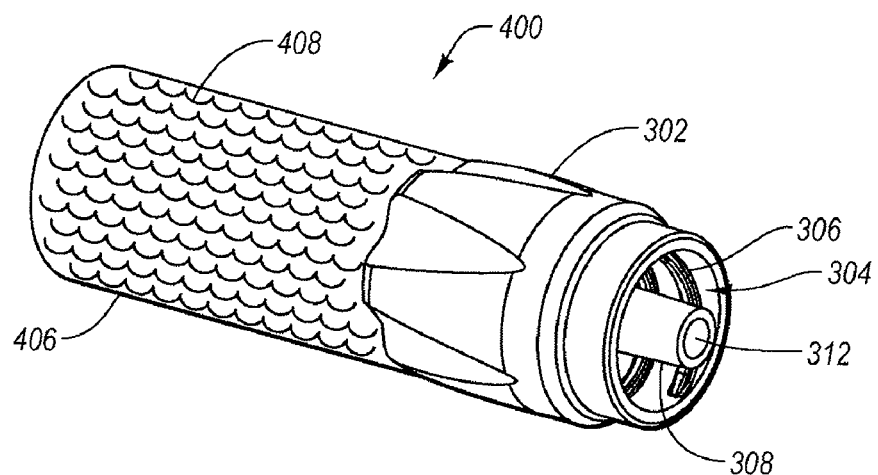
FIG. 21 is a perspective view of a cap assembly having a cap, similar to the cap seen in FIG. 20, and a fluid reservoir coupled thereto.
Figure 22:
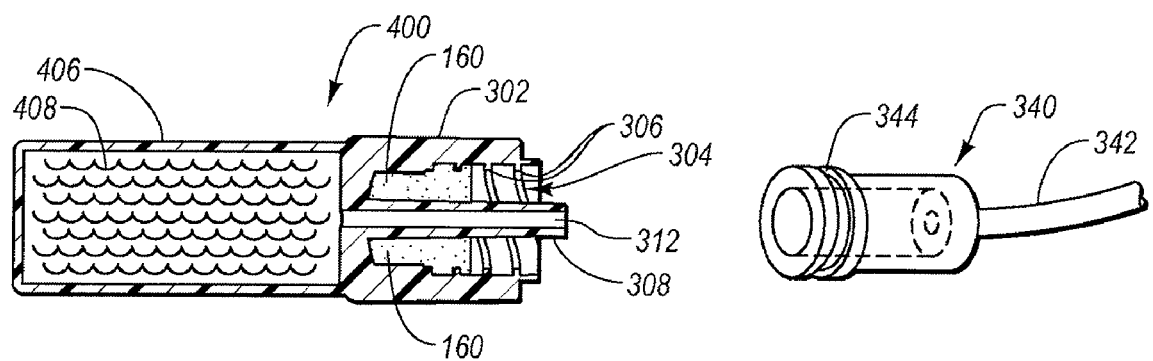
FIG. 22 is a cross-sectional view of the cap assembly seen in FIG. 21 with an associated medical connector about to be connected thereto.

Attention is now directed to FIGS. 21 and 22 in which an exemplary embodiment of a cap assembly 400 is illustrated. Cap assembly 400 includes cap 302 and a fluid reservoir 406 coupled to one end thereof. As described above, post 308 of cap 302 includes a channel 312 extending therethrough. Channel 312 is sized and shaped to connect to a female luer access device ("LAD") to open the fluid pathway. Channel 312 provides a fluid passageway through cap 302 to enable fluid to flow between fluid reservoir 406 and fluid pathway 342. For example, cap assembly 400 can be employed to administer a medication to a patient through fluid pathway 342. Specifically, fluid reservoir 406 can contain a liquid medication that is released into fluid pathway 342 when cap assembly 400 is coupled to connector 340. Cap assembly 400 can also be employed to cleanse and disinfect fluid pathway 342. In particular, fluid reservoir 406 can contain an antiseptic agent that is released into fluid pathway 342 when cap assembly 400 is coupled to connector 340.

In some embodiments of cap assembly 400, a seal or valve is disposed within channel 312. The seal or valve can be adapted to retain fluid 408, such as an antiseptic solution or medication, within fluid reservoir 406 until cap assembly 400 is securely coupled to a medical connector, such as connector 340. When cap assembly 400 is coupled to connector 340, the seal can be broken or the valve can be opened to allow fluid 408 to flow through channel 312 and into fluid pathway 342.

Cap assembly 400 can be configured to diffuse fluid 408 from fluid reservoir 406 into fluid pathway 342 over time as long as fluid 408 has a higher concentration than the fluid within fluid pathway 342. For example, if fluid 408 has a significantly higher concentration level than the fluid within fluid pathway 342, fluid 408 will diffuse into fluid pathway 342 more rapidly. In contrast, if fluid 408 has a concentration level only slightly higher than the fluid within fluid pathway 342, fluid 408 will diffuse into fluid pathway 342 more slowly. Thus, medication can be administered by a physician, or an antiseptic agent can be diffused into fluid pathway 342 over time to reduce or eliminate the existence of microorganisms within fluid pathway 342.

Attention is now directed to FIGS. 23-29, in which alternative embodiments of fluid reservoirs are illustrated for cap assemblies according to the present invention. For example, in FIG. 23 a cap assembly 500 is illustrated, which includes cap 302, as described above, and fluid bulb 506. Cap assembly 500 can be employed to administer a medication to a patient through a fluid pathway, such as a central line. Specifically, fluid bulb 506 can contain a liquid medication that is released into a fluid pathway when cap assembly 500 is coupled to a medical connector. Cap assembly 500 can also be employed to cleanse and disinfect the fluid pathway. In particular, fluid bulb 506 can contain an antiseptic agent that is released into a fluid pathway when cap assembly 500 is coupled to a medical connector.

Figure 23:
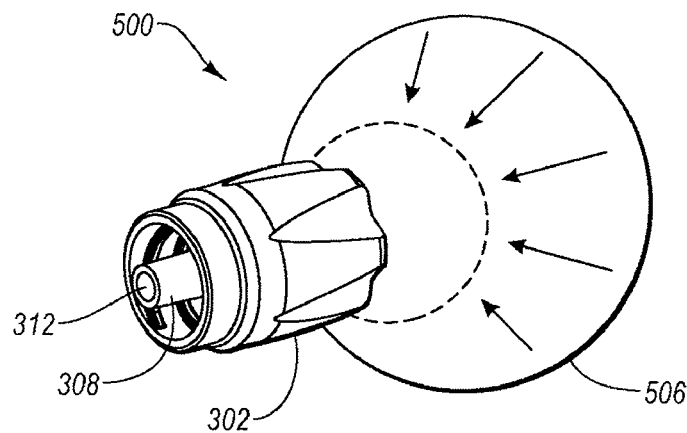
FIG. 23 is a perspective view of an another embodiment of a cap assembly according to the present invention, wherein the fluid reservoir comprises an elastomeric bulb.

In the embodiment illustrated in FIG. 23, fluid bulb 506 is an elastomeric bulb. During manufacture of cap assembly 500, fluid bulb 506 is filled with a fluid, such as an antiseptic or medicine, so that fluid bulb 506 is expanded to the size illustrated in FIG. 23. The elastomeric properties of fluid bulb 506 cause fluid bulb 506 to contract in the direction of the illustrated arrows, thereby applying pressure on the fluid within fluid bulb 506. However, a seal or valve can be disposed within channel 312 of cap 302 to retain the fluid within fluid bulb 506, thereby preventing fluid bulb 506 from fully contracting back to its normal size (illustrated in dashed lines in FIG. 23). Nevertheless, once cap assembly 500 is securely coupled to a medical connector, the seal or valve within channel 312 can be activated, allowing fluid bulb 506 to fully contract to its natural size (illustrated in dashed lines in FIG. 23), thereby forcing the fluid within fluid bulb 506 through channel 312 and into a fluid pathway connected to cap assembly 500. As discussed elsewhere herein, a valve disposed within channel 312 can also be adapted to prevent fluid from undesirably refluxing into fluid bulb 506. In particular, the valve can be a one-way valve, a duckbill valve, a back check valve, a pressure activated valve, or the like to prevent fluid from flowing from a fluid pathway into fluid bulb 506. It will be appreciated however, that in some embodiments, a valve or seal is not disposed within channel 312.

Figure 24:
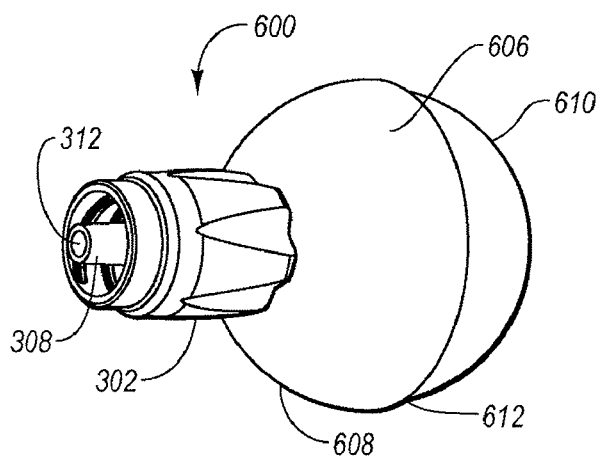
FIG. 24 is a perspective view of yet another embodiment of a cap assembly according to the present invention, wherein the fluid reservoir comprises a deformable fluid bulb.
Figure 25:
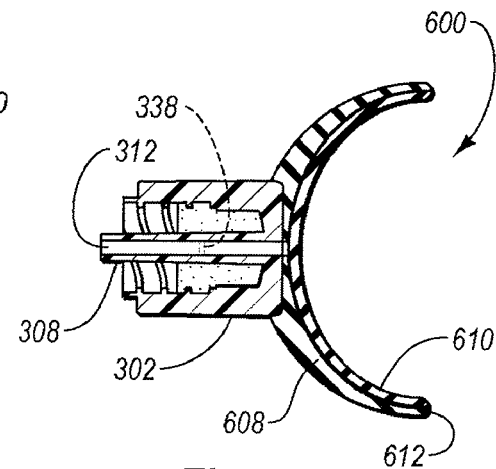
FIG. 25 is a cross-sectional view of the cap assembly seen in FIG. 24 with a portion of the fluid bulb inverted to dispense fluid from the fluid reservoir.

FIGS. 24 and 25 depict a cap assembly 600 that is similar to cap assembly 500. In particular, cap assembly 600 includes cap 302 and a fluid bulb 606 coupled to one end thereof. Fluid bulb 606 includes a fixed, thick wall portion 608, a collapsible, thin wall portion 610, and a hinge 612 that joins fixed wall 608 and collapsible wall 610. In the illustrated embodiment, fixed wall 608 is coupled to cap 302. It will be appreciated, however, that collapsible wall 610 can be coupled to cap 302 without departing from the scope of the present invention.

Hinge 612 can be a "living hinge" adapted to enable collapsible wall 610 to be inverted as shown in FIG. 25 in order to dispense fluid from within fluid bulb 606. In particular, collapsible wall 610 can be pressed toward cap 302, thereby forcing fluid within fluid bulb 606 to be dispensed through channel 312. Additionally, thick wall 608 and collapsible wall 610 can be sized and shaped such that collapsible wall 610 nests within thick wall 608 when collapsible wall 610 is inverted as shown in FIG. 25. Moreover, collapsible wall 610 can be formed such that once collapsible wall 610 is inverted within thick wall 608, collapsible wall 610 remains inverted within thick wall 608 and does not right itself. Maintaining collapsible wall 610 in the inverted position prevents a vacuum from forming within fluid bulb 606, in turn preventing fluid from undesirably refluxing into fluid bulb 606. These features of fluid bulb 606 can be realized by selecting the appropriate dimensions for thick wall 608 and collapsible wall 610, as well as the material used to manufacture fluid bulb 606. Fluid bulb 606 can be formed of a polymer material, such as polyethylene or polypropylene, to provide it with the functional characteristics described above.

In some embodiments of cap assembly 600, a seal or valve is disposed within channel 312. The seal or valve can be adapted to retain fluid, such as an antiseptic solution or medication, within fluid reservoir 606 until cap assembly 600 is securely coupled to a medical connector. Once cap assembly 600 is securely coupled to a medical connector, the seal can be broken or the valve can be opened to allow fluid to flow through channel 312 and into fluid pathway. The valve can also be adapted to prevent fluid from undesirably refluxing into fluid reservoir 606. In particular, the valve can be a one-way valve, a duckbill valve, a back check valve, a pressure activated valve, or the like. While the illustrated embodiment of cap assembly 500 includes a valve 338 disposed within channel 312, it will be appreciated, however, that in some embodiments, a valve or seal is not disposed within channel 312.

As appreciated by one of ordinary skill in the art, it can be undesirable to introduce air into a fluid pathway associated with a patient, such as a central line or catheter. In order to reduce the amount of air introduced into a fluid pathway with a syringe, for example, a medical professional, such as a doctor or nurse, will prime the syringe to remove excess air therefrom. Priming a syringe can be accomplished with three steps. First, the syringe is held with the needle or evacuation channel pointing vertically upward to cause air within the syringe to move toward the needle or evacuation channel. Second, tapping on the side of the syringe helps release air bubbles disposed on the interior surface of the syringe, thereby allowing the air bubbles to move towards the needle or evacuation channel. Finally, compressing the plunger dispenses the air through the needle or evacuation channel prior to injecting the fluid within the syringe into a fluid pathway.

A similar procedure can be used to prime the cap assemblies of the present invention. Additionally, the cap assemblies of the present invention can also include various features that reduce or eliminate the transfer of air within the fluid bulb into a fluid pathway. While these features will be described with respect to the cap assembly embodiment illustrated in FIG. 26, it will be appreciated that these features can be incorporated into any of the cap assembly embodiments described herein.

Figure 26:
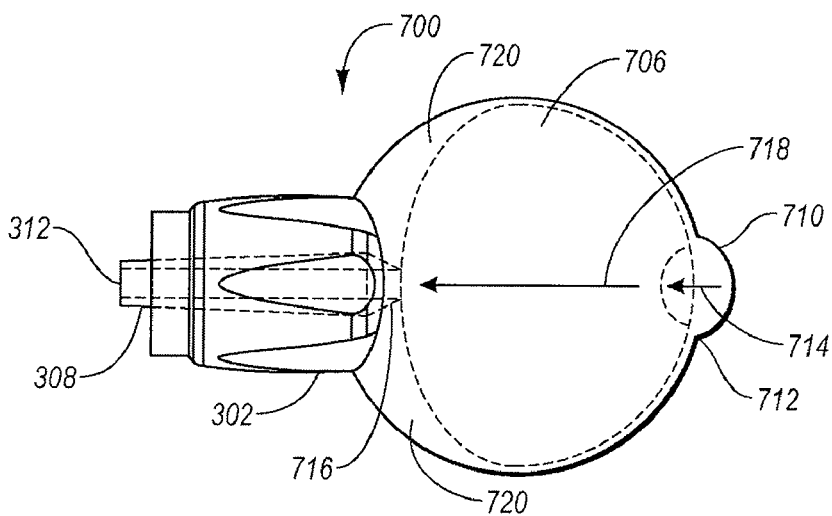
FIG. 26 is a side view of a cap assembly according to the present invention, having a primer bulb and a secondary post to reduce the amount of air introduced into a fluid pathway.

With attention to FIG. 26, another exemplary embodiment of a cap assembly, generally denoted at 700, is illustrated. Cap assembly 700 is similar to cap assemblies 400, 500, and 600 described herein. In particular, cap assembly 700 includes cap 302 and a fluid bulb 706. Fluid bulb 706 can be an elastomeric bulb, such as fluid bulb 506, or a fluid bulb with a "living hinge," such as fluid bulb 606. Alternatively, fluid bulb 706 can be a fluid reservoir similar to fluid reservoir 406. Additionally, cap assembly 700 includes a primer bulb 710 to help reduce or eliminate the amount of air transferred from fluid bulb 706 to a fluid pathway. Primer bulb 710 is joined to fluid bulb 706 by a hinge 712. Hinge 712 can be a "living hinge" adapted to enable primer bulb 710 to be inverted in the direction of arrow 714 in order to evacuate air from within fluid bulb 706 in a manner similar to the compression of a syringe plunger, as described herein. In particular, cap assembly 700 can be held with cap 302 positioned vertically above fluid bulb 706 to cause air within fluid bulb 706 to move toward channel 312. A medical professional can tap on fluid bulb 706 to cause any air bubbles to be released from the interior surface of fluid bulb 706 and move toward channel 312. Primer bulb 710 can then be pressed in the direction of arrow 714 toward cap 302, thereby forcing air within fluid bulb 706 to be evacuated through channel 312.

Furthermore, cap assembly 700 includes a secondary post 716 to help reduce or eliminate the amount of air transferred from fluid bulb 706 to a fluid pathway. In the illustrated embodiment, secondary post 716 comprises part of cap 302 and is a shortened mirror image of post 308. In other words, secondary post 716 is a frustoconical cone shaped post that extends from cap 302 partially into fluid bulb 706. Channel 312 extends through secondary post 716 so as to create a fluid passageway through cap 302. Secondary post 716 extends partially into fluid bulb 706 so that when fluid bulb 706 is fully compressed in the direction of arrow 718, there remains an air entrapment chamber 720 within fluid bulb 706. As will be appreciated, air bubbles within fluid bulb 706 will be disposed on the interior surface of fluid bulb 706. As fluid bulb 706 is compressed in the direction of arrow 718, the air bubbles will be forced along the interior surface of fluid bulb 706 toward secondary post 716. The air bubbles will accumulate within air entrapment chamber 720, thereby preventing the air bubbles from being evacuated through channel 312.

Similar to fluid bulb 606, fluid bulb 706 and primer bulb 710 can be formed such that once inverted, primer bulb 710 and fluid bulb 706 remain inverted and do not right themselves. Maintaining primer bulb 710 and fluid bulb 706 in the inverted position prevents a vacuum from forming within fluid bulb 706, in turn preventing fluid from undesirably refluxing into fluid bulb 706. These features of primer bulb 710 and fluid bulb 706 can be realized by selecting the appropriate dimensions for primer bulb 710 and fluid bulb 706, as well as the material used to manufacture primer bulb 710 and fluid bulb 706. Primer bulb 710 and fluid bulb 706 can be formed of a polymer material, such as polyethylene or polypropylene, to provide the functional characteristics described above.

Figure 27:
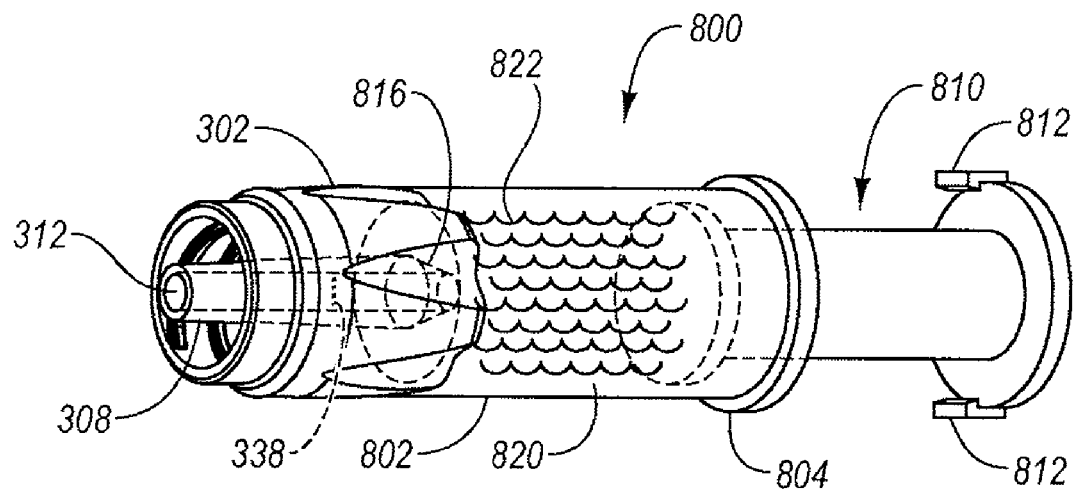
FIG. 27 is a perspective view of still yet another cap assembly according to the present invention, having an evacuable fluid chamber coupled thereto, the fluid chamber having a barrel and plunger configuration.
Figure 28:
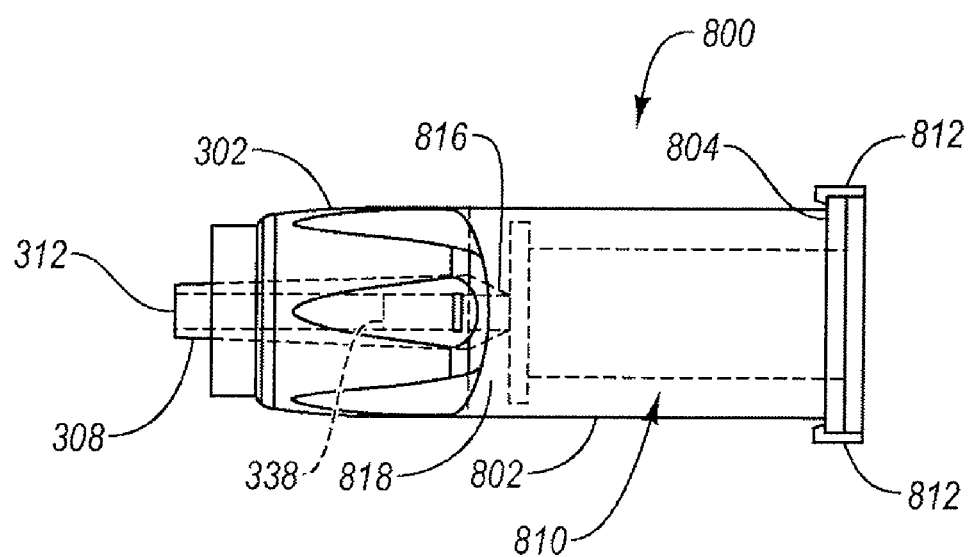
FIG. 28 is a side view of the cap assembly seen in FIG. 26, with the plunger portion fully compressed.

FIGS. 27 and 28 illustrate yet another exemplary embodiment of a cap assembly, generally denoted at 800, according to the present invention. Cap assembly 800 includes cap 302, barrel 802, and plunger 810. Barrel 802 can be joined to cap 302 in any suitable manner, including with the use of an adhesive, such as glue, a mechanical fastener, or a friction fitting. Cap 302 and barrel 802 can be formed as an integral piece. It will be appreciated that barrel 802 can be permanently joined to cap 302, or barrel 802 can be removably joined to cap 302. Plunger 810 is movably coupled to barrel 802. In particular, a first end of plunger 810 is inserted within barrel 802, and creates a seal between the plunger 810 and the interior surface of barrel 802.

In the illustrated embodiment, barrel 802 includes a fluid chamber 820 that is filled with an antiseptic agent or medicine 822. Fluid chamber 820 is defined by the internal surface of barrel 802, cap 302, and the first end of plunger 810. Plunger 810 can be depressed to force fluid 822 through channel 312 and into a fluid pathway. Continued movement of plunger 810 in the direction of cap 302 decreases the internal volume of fluid chamber 820, thereby forcing fluid 822 through channel 312 and into a fluid pathway.

Cap assembly 800 can be equipped with gauges, guides, or other indicator means to assist a medical profession in determining the amount of fluid 822 that has been forced out of cap assembly 800 and into a fluid pathway. For instance, if fluid 822 is a medicine that is administered to a patient incrementally, cap assembly 800 can be equipped with a gauge, guide, or other indicator means that indicates to a medical professional how much of fluid 822 has been administered. For example, barrel 802 can include labels or other markings that correspond to the position of plunger 810 relative to barrel 802 and the internal volume of fluid chamber 820. Thus, as a medical professional depresses plunger 810, the leading edge of plunger 810 will be positioned adjacent one of the labels or other markings on barrel 802, thereby indicating the amount of fluid 822 that has been administered and/or the amount of fluid 822 remaining within fluid chamber 820. Likewise, fluid chamber 820 can be equipped with audible and/or tactile indicator means that indicate to a medical professional the amount plunger 910 has been depressed, which corresponds to the amount of fluid 822 that has been administered. Thus, cap assembly 800 can be adapted to provide incremental dosages to a patient. Furthermore, cap assembly 800 includes a locking mechanism to prevent reflux of fluid into fluid chamber 820. The locking mechanism of cap assembly 800 includes a locking ridge 804 and at least one latch 812. In the illustrated embodiment, latches 812 are formed as part of plunger 810, and locking ridge extends around the end of barrel 802. In use, plunger 810 is depressed to dispense fluid 822 from fluid chamber 820. When plunger 810 is fully depressed, latches 812 engage locking ridge 804 to prevent plunger 810 from being withdrawn from barrel 802. Because the first end of plunger 810 sealingly engages the interior surface of barrel 802, withdrawing plunger 810 from within barrel 802 could create a vacuum at within barrel 802, thereby drawing fluid from a fluid pathway into barrel 802. To reduce or eliminate such reflux, latches 812 engage locking ridge 804 to prevent the withdrawal of plunger 810 from barrel 802. Additionally, or alternatively, a valve 338 can be disposed within channel 312 to prevent undesirable reflux of fluid into fluid chamber 820. In particular, the valve can be a one-way valve, a duckbill valve, a back check valve, a pressure activated valve, or the like. While the illustrated embodiment of cap assembly 800 includes a valve 338 disposed within channel 312, it will be appreciated, however, that in some embodiments, a valve or seal is not disposed within channel 312. Similar to cap assembly 700, cap assembly 800 can also include a secondary post 816 to help reduce or eliminate the amount of air transferred from fluid chamber 820 to a fluid pathway. In the illustrated embodiment, secondary post 816 comprises part of cap 302 and is a shortened mirror image of post 308. In other words, secondary post 816 is a frustoconical cone shaped post that extends from cap 302 partially into fluid chamber 820. Channel 312 extends through secondary post 816 so as to create a fluid passageway through cap 302. Secondary post 816 extends partially into fluid chamber 820 so that when plunger 810 is fully depressed there remains an air entrapment chamber 818 within fluid chamber 820. As will be appreciated, air bubbles within fluid chamber 820 will be disposed on the interior surface of fluid chamber 820. As plunger 810 is depressed, the air bubbles will be forced along the interior surface of fluid chamber 820 toward secondary post 816. The air bubbles will accumulate within air entrapment chamber 818, thereby preventing the air bubbles from being dispensed through channel 312.

Figure 29:
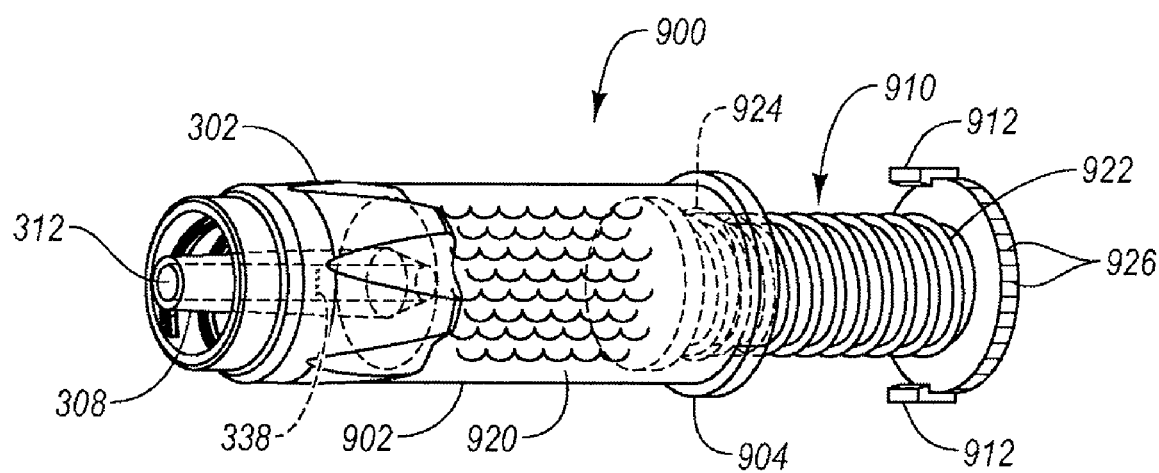
FIG. 29 is a perspective view of a cap assembly, similar to the cap assembly seen in FIGS. 27 and 28, but the plunger and barrel are threadably engaged.

FIG. 29 illustrates a cap assembly 900, similar to cap assembly 800. In particular, cap assembly 900 includes cap 302, barrel 902, and plunger 910. Barrel 902 is joined to cap 302 in any suitable manner, including with the use of an adhesive, such as glue, a mechanical fastener, or a friction fitting. Alternatively, cap 302 and barrel 902 can be formed as an integral piece. Plunger 910 is movably coupled to barrel 902. In particular, a first end of plunger 910 is inserted within barrel 902, and creates a seal between the plunger 910 and the interior surface of barrel 902. Further, plunger 910 includes threads 922 disposed on an exterior surface thereof and barrel 902 includes threads 924 disposed on an interior surface thereof. Thread 922 and 924 are adapted to engage one another such that rotation of plunger 910 relative to barrel 902 causes plunger 910 to be drawn into barrel 902. The end of plunger 910 also includes ridges 926 to facilitate gripping and rotation of plunger 910.

In the illustrated embodiment, barrel 902 includes a fluid chamber 920 that is filled with an antiseptic agent or medicine 22. Fluid chamber 920 is defined by the internal surface of barrel 902, cap 302, and the first end of plunger 910. Plunger 910 can be rotated relative to barrel 902 to force fluid 922 through channel 312 and into a fluid pathway. Continued rotation of plunger 910 decreases the internal volume of fluid chamber 920, thereby forcing fluid 922 through channel 312 and into a fluid pathway.

Furthermore, cap assembly 900 includes a locking mechanism to prevent reflux of fluid into fluid chamber 920. The locking mechanism of cap assembly 900 includes a locking ridge 904 and at least one latch 912. In the illustrated embodiment, latches 912 are formed as part of plunger 910, and locking ridge extends around the end of barrel 902. In use, plunger 910 is rotated relative to barrel 902 to dispense fluid 922 from fluid chamber 920. When plunger 910 is fully rotated, latches 912 engage locking ridge 904 to prevent plunger 910 from being withdrawn from barrel 902. Because the first end of plunger 910 sealingly engages the interior surface of barrel 902, withdrawing plunger 910 from within barrel 902 could create a vacuum within barrel 902, thereby drawing fluid from a fluid pathway into barrel 902. To reduce or eliminate such reflux, latches 912 engage locking ridge 904 to prevent the withdrawal of plunger 910 from barrel 902. Additionally, or alternatively, a valve 338 can be disposed within channel 312 to prevent undesirable reflux of fluid into fluid chamber 920. In particular, the valve can be a one-way valve, a duckbill valve, a back check valve, a pressure activated valve, or the like. While the illustrated embodiment of cap assembly 900 includes a valve 338 disposed within channel 312, it will be appreciated, however, that in some embodiments, a valve or seal is not disposed within channel 312.

The caps described herein can be formed of, or coated with various colored materials or coatings. In one exemplary embodiment, the caps comprise a single color. Alternatively, each cap can be a separate color. Coloring the caps can provide various advantages, such as ready identification of the type of cap, ready matching of a particularly colored cap with a particular type of medical connector, and the like.

The inventions disclosed herein may be embodied in other specific forms without departing from the spirit or essential characteristics thereof. The present embodiments are therefore to be considered in all respects as illustrative and not restrictive. The scope of the invention is, therefore, indicated by the appended claims rather than by the foregoing description. All changes which come within the meaning and range of equivalency of the claims are therefore intended to be embraced within their scope.

What is claimed is:

1. A method of applying an antiseptic agent to a medical connection having a male luer connector and a needleless injection site, the method comprising:
    providing an assembly comprising
        a male-disinfecting cap including a receiving portion having (i) a single opening in which a male luer connector can be received, (ii) an exterior surface having a recess disposed about an outer circumference thereof and (iii) an antiseptic agent;
        a female-disinfecting cap including a receiving portion having (i) a single opening in which a needleless injection site can be received, (ii) an exterior surface having a recess disposed about an outer circumference thereof, and (iii) an antiseptic agent; and
        a seal disposed around and in contact with both the recess of the exterior surface of the male-disinfecting cap and the recess of the exterior surface of the female-disinfecting cap and linking the male-disinfecting cap to the female-disinfecting cap;
    separating the male-disinfecting cap from the assembly;
    inserting the male luer connector into the receiving portion of the male-disinfecting cap so as to transfer at least some of the antiseptic agent to at least a surface of the male luer connector;
    separating the female-disinfecting cap from the assembly; and
    inserting the needleless injection site into the receiving portion of the female-disinfecting cap so as to transfer at least some of the antiseptic agent to at least a surface of the needleless injection site.

2. The method of claim 1, wherein the assembly further comprises a pad.

3. The method of claim 2, wherein the pad is disposed within the receiving portion of the male-disinfecting cap.

4. The method of claim 3, further comprising scrubbing the male luer connector with the pad.

5. The method of claim 1, wherein separating one cap from the assembly comprises rotating the male-disinfecting cap relative to the female-disinfecting cap.

6. The method of claim 1, wherein the male-disinfecting cap comprises threading, the method further comprising engaging the threading of the male-disinfecting cap into the threading of the male luer connector.

7. A method of applying an antiseptic agent to a medical connection having a male luer connector and a needleless injection site, the method comprising:
    providing an assembly comprising
        a male-disinfecting cap having an interior portion with a single opening and an exterior surface having a recess disposed about an outer circumference thereof;
        a first pad having an antiseptic agent and disposed within the interior portion of the male-disinfecting cap;
        a female-disinfecting cap having an interior portion with a single opening and an exterior surface having a recess disposed about an outer circumference thereof;
        a second pad having an antiseptic agent and disposed within the interior portion of the female-disinfecting cap; and
        a seal disposed around and in contact with both the recess of the male-disinfecting cap and the recess exterior of the female-disinfecting cap and linking the male-disinfecting cap and female-disinfecting cap;
    separating the male-disinfecting cap from the assembly;
    inserting the male luer connector into the interior portion of the male-disinfecting cap so as to transfer at least some of the antiseptic agent of the first pad to at least a surface of the male luer connector;
    separating the female-disinfecting cap from the assembly; and
    inserting a needleless injection site into the interior portion of the female-disinfecting cap so as to transfer at least some of the antiseptic agent of the second pad to at least a surface of the needleless injection site.

8. The method of claim 7, wherein in the assembly, a portion of the male-disinfecting cap is nested within the female-disinfecting cap.

9. The method of claim 7, further comprising scrubbing the needleless injection site with the second pad.

10. The method of claim 7, wherein the male-disinfecting cap comprises threading, the method further comprising engaging the threading into threading of the male luer connector.

* * * * *